(12) United States Patent
Gojon-Zorrilla et al.

(10) Patent No.: US 10,849,872 B2
(45) Date of Patent: Dec. 1, 2020

(54) METHODS AND COMPOSITIONS FOR TREATING OBESITY, PREVENTING WEIGHT GAIN, PROMOTING WEIGHT LOSS, PROMOTING SLIMMING, OR TREATING OR PREVENTING THE DEVELOPMENT OF DIABETES

(71) Applicant: NAN Global, LLC, Wilmington, DE (US)

(72) Inventors: Gabriel Gojon-Zorrilla, San Pedro Garza García (MX); Gabriel Gojon-Romanillos, San Pedro Garza García (MX)

(73) Assignee: NAN Global, LLC, Wilmington, DE (US)

( * ) Notice: Subject to any disclaimer, the term of this patent is extended or adjusted under 35 U.S.C. 154(b) by 0 days.

(21) Appl. No.: 14/790,824

(22) Filed: Jul. 2, 2015

(65) Prior Publication Data
US 2016/0000745 A1    Jan. 7, 2016

Related U.S. Application Data

(60) Provisional application No. 62/127,111, filed on Mar. 2, 2015, provisional application No. 62/020,797, filed on Jul. 3, 2014.

(51) Int. Cl.
| | | |
|---|---|---|
| *A61K 31/205* | (2006.01) | |
| *A61K 31/277* | (2006.01) | |
| *A61K 45/06* | (2006.01) | |

(52) U.S. Cl.
CPC .......... *A61K 31/277* (2013.01); *A61K 31/205* (2013.01); *A61K 45/06* (2013.01)

(58) Field of Classification Search
None
See application file for complete search history.

(56) References Cited

U.S. PATENT DOCUMENTS

| 3,810,994 | A | 5/1974 | Wiegand |
| 2004/0138301 | A1 | 7/2004 | Hansen et al. |
| 2008/0262093 | A1 | 10/2008 | Spiegelman |
| 2011/0244059 | A1 | 10/2011 | Jin |
| 2012/0270814 | A1 | 10/2012 | Pan |

FOREIGN PATENT DOCUMENTS

| RU | 2290397 | C2 | 12/2006 |
| RU | 2342115 | C2 | 12/2008 |

OTHER PUBLICATIONS

Kamal et al., Diabetology & Metabolic Syndrome 2009, 1:17, pp. 1-14.*
Kalpana et al., International Journal of Scientific and Research Publications, vol. 2, Issue 9, 2012, pp. 1-5.*
Andrea O. Schaffhauser, Ann Nutr Metab 2000;44:94-96.*
Gazit et al., "Tyrphostins I: synthesis and biological activity of protein tyrosine kinase inhibitors," J Med Chem. 32(10):2344-52 (1989).
International Search Report and Written Opinion for International Application No. PCT/US2015/039075, dated Jan. 8, 2016 (13 pages).
Elmslie et al., "Carnitine does not improve weight loss outcomes in valproate-treated bipolar patients consuming an energy-restricted, low-fat diet," Bipolar Disord. 8(5 Pt 1):503-7 (2006).
Gawrylewski, "The trouble with animal models," The Scientist Magazine, <https://www.the-scientist.com/?articles.view/articleNo/25184/title/The-Trouble-with-Animal-Models/>, published Jul. 1, 2007, retrieved Dec. 1, 2017 (5 pages).
Goldgof et al., "The chemical uncoupler 2,4-dinitrophenol (DNP) protects against diet-induced obesity and improves energy homeostasis in mice at thermoneutrality," J Biol Chem. 289(28):19341-50 (2014) (11 pages).
Lofgren et al., "Weight loss associated with reduced intake of carbohydrate reduces the atherogenicity of LDL in premenopausal women," Metabolism. 54(9):1133-41 (2005).
Malaguarnera et al., "L-Carnitine supplementation reduces oxidized LDL cholesterol in patients with diabetes," Am J Clin Nutr. 89(1):71-6 (2009).
Martin et al., "'Control' laboratory rodents are metabolically morbid: why it matters," Proc Natl Acad Sci U.S.A. 107(14):6127-33 (2010).
Odo et al., "A pilot clinical trial on L-carnitine supplementation in combination with motivation training: effects on weight management in healthy volunteers," Food and Nutrition Sciences. 4:222-31 (2013).
Poddar et al., "Nutraceutical supplements for weight loss: a systematic review," Nutr Clin Pract. 26(5):539-52 (2011) (16 pages).
Pooyandjoo et al., "The effect of (L-)carnitine on weight loss in adults: a systematic review and meta-analysis of randomized controlled trials," Obes Rev. 17(10):970-6 (2016).
Ruxton et al., "A review of the efficacy and safety of key ingredients of over-the-counter products for weight management," British Food Journal. 107(2):111-25 (2005) (17 pages).
Seok et al., "Genomic responses in mouse models poorly mimic human inflammatory diseases," Proc Natl Acad Sci U.S.A. 110(9):3507-12 (2013).
Servick, "Mouse microbes may make scientific studies harder to replicate," Science, <http://www.sciencemag.org/news/2016/08/mouse-microbes-may-make-scientific-studies-harder-replicate>, published Aug. 16, 2016, retrieved Dec. 19, 2017 (8 pages).
Van der Worp et al., "Can animal models of disease reliably inform human studies?," PLoS Med. 7(3):e1000245 (2010).

(Continued)

*Primary Examiner* — Shobha Kantamneni
(74) *Attorney, Agent, or Firm* — Clark & Elbing LLP

(57) ABSTRACT

The present invention relates to compositions and kits including a chemical uncoupler, such as tyrphostin 9 or precursor or a salt thereof, and compositions including a chemical uncoupler, such as tyrphostin 9 in combination with one or more therapeutic agents, for example, L-carnitine, which are useful, for example, in treating obesity, preventing weight gain, promoting weight loss/slimming, and/or treating or preventing the development of diabetes.

3 Claims, No Drawings

(56) References Cited

OTHER PUBLICATIONS

Villani et al., "L-Carnitine supplementation combined with aerobic training does not promote weight loss in moderately obese women," Int J Sport Nutr Exerc Metab. 10(2):199-207 (2000).
Abstract for Paulson et al., "The beneficial effects of L Carnitine in Diabetes Mellitus," Federation Proceedings, Federation of American Societies for Experimental Biology. 41:4 (1982).
Abstract for Albanese et al., "Fat mass loss in obese subjects treated with carnitine: a whole body DXA evaluation," Journal of Bonne and Mineral Rese, 20(9):S218 (2005).
Extended European Search Report for European Patent Application No. 15815585.3, dated Mar. 14, 2018 (11 pages).
International Preliminary Report on Patentability and Written Opinion of the International Searching Authority for International Patent Application No. PCT/US2015/039075, dated Jan. 3, 2017 (10 pages).
Melton et al. "L-carnitine supplementation does not promote weight loss in ovariectomized Rats despite endurance exercise," Int J Vitam Nutr Res Suppl. 75(2): 156-160 (2005).
Brandsch et al. "Effect of L-Carnitine on Weight Loss and Body Composition of Rats Fed a Hypocaloric Diet," Ann Nutr Metab. 46(5):205-210, (2002).
Sawicka et al. "L-Carnitine Supplementation in Older Women. A Pilot Study on Aging Skeletal Muscle Mass and Function," Nutrients. 10(55) 2018.
Del Vecchio et al. "Comment on The effect of (L-)carnitine on weight loss in adults: a systematic review on meta-analsis of randomized controlled trials," Obes Rev. 18(2):277-8 (2017).
Search Report for Russian Patent Application No. 2017103450, dated Feb. 12, 2019 (5 pages).
Office Action for Russian Patent Application No. 2017103450, dated Feb. 13, 2019 (22 pages).

* cited by examiner

METHODS AND COMPOSITIONS FOR TREATING OBESITY, PREVENTING WEIGHT GAIN, PROMOTING WEIGHT LOSS, PROMOTING SLIMMING, OR TREATING OR PREVENTING THE DEVELOPMENT OF DIABETES

BACKGROUND OF THE INVENTION

The present invention relates to methods, compositions, and kits for the treatment and prevention of diabetes and weight gain.

Obesity and the resulting metabolic syndrome, including diabetes, are serious threats to current and future global health. The medical condition of obesity increases the likelihood of premature death and various diseases in addition to diabetes, such as heart disease, obstructive sleep apnea, osteoarthritis, hypertension, dyslipidemia, and certain types of cancer. The World Health Organization formally recognized obesity as a global epidemic in 1997, and more than 63 million people worldwide struggle with the challenge of managing both obesity and diabetes. Furthermore, globally, the estimated healthcare expenditures to both treat and prevent diabetes are expected to increase from approximately $548 billion U.S. dollars in 2013 to approximately $627 billion U.S. dollars by 2035.

There is a lack of effective, convenient, and safe treatments that promote weight loss, reduce weight gain, or prevent the development of diabetes in the vast number of individuals for which modifications of exercise and diet are not feasible treatments. Obesity and diabetes are related disorders that share impairments in both cellular and metabolic processes; in fact, about 90% of obese patients are also diabetic. Individuals with obesity and/or diabetes often struggle with high triglyceride levels in blood plasma. Another hallmark of such metabolic disorders are fluctuating blood glucose levels that may rapidly increase for a prolonged period. Treatments which efficaciously decrease blood triglyceride levels and stabilize blood glucose levels in such patients are thus highly desirable.

In light of the increasing prevalence of obesity and diabetes combined with the resulting health and financial consequences, the prevention and treatment of these metabolic disorders are paramount for the future of global health. Thus, there is a need for affordable and safe pharmacological interventions that prevent or treat obesity and diabetes, and which effectively normalize blood glucose and lipid levels. Furthermore, convenient methods of producing the required compounds and compositions of matter are highly advantageous for pharmaceutical purposes.

SUMMARY OF THE INVENTION

A first aspect of the invention features a method for treating obesity, preventing weight gain, promoting weight loss, promoting slimming, and/or treating or preventing the development of diabetes, the method including administering to a subject in need thereof a chemical uncoupler or precursor or salt or precursor thereof and L-carnitine or derivative or salt or precursor thereof, such that the chemical uncoupler or precursor or salt thereof and L-carnitine or derivative or salt thereof are in therapeutically or prophylactically effective amounts to treat obesity, prevent weight gain, promote weight loss, promote slimming, or treat or prevent the development of diabetes. Desirably, the chemical uncoupler or precursor or salt thereof and the L-carnitine or derivative or salt thereof are in a composition formulated for oral, topical, or parenteral administration.

In some embodiments, the chemical uncoupler or precursor or salt thereof and the L-carnitine or derivative or salt thereof are administered substantially simultaneously (e.g., in combination) or within one hour of each other. In other embodiments, the chemical uncoupler or precursor or salt thereof and the L-carnitine or derivative or salt thereof are administered sequentially (e.g., within one hour, two hours, three hours, four hours, five hours, six hours, seven hours, eight hours, nine hours, ten hours of each other, etc.).

In various embodiments, the chemical uncoupler or precursor or salt thereof is a compound from Table 1. In certain embodiments, the chemical uncoupler is tyrphostin 9.

In preferred embodiments, tyrphostin 9 is present in an amount from about 2 mg to about 200 mg and L-carnitine is present in an amount from about 50 mg to about 5000 mg. In certain embodiments, tyrphostin 9 is present in an amount of about 10 mg and the L-carnitine is present in an amount of about 700 mg. In preferred embodiments, tyrphostin 9 is present in an amount of about 5 mg to about 10 mg and the L-carnitine is present in an amount of about 700 mg.

A second aspect of the invention features a method for treating obesity, preventing weight gain, promoting weight loss, promoting slimming, or treating or preventing the development of diabetes, the method including orally administering to a subject in need thereof a composition including a chemical uncoupler or precursor or salt thereof in an amount from about 2 mg to about 200 mg, such that the composition is effective to treat obesity, prevent weight gain, promote weight loss, promote slimming, or treat or prevent the development of diabetes in the subject.

Desirably, the unit dosage form of the composition is a capsule or tablet. In various embodiments, the chemical uncoupler or precursor or salt thereof is a compound from Table 1. In preferred embodiments, the chemical uncoupler is tyrphostin 9 or a salt thereof or a derivative or precursor thereof.

In some embodiments, the method may further include administering one or more therapeutic agent(s) selected from the group consisting of insulin, a sulfonylurea, a biguanide, an alpha-glucosidase inhibitor, a thiazolidinedione, a meglitinide, an antidiabetic agent, a statin, and a weight loss supplement.

In certain embodiments, the chemical uncoupler or precursor or salt thereof and the L-carnitine or derivative or salt thereof, or the composition, which includes only a chemical uncoupler, preferably tyrphostin 9, is administered one or more times a day. In further embodiments, the chemical uncoupler or precursor or salt thereof and the L-carnitine or derivative or salt thereof, or the composition, which includes only a chemical uncoupler, is administered for at least two to thirty days. In other embodiments, the chemical uncoupler or precursor or salt thereof and the L-carnitine or derivative or salt thereof, or the composition which includes only a chemical uncoupler is administered for more than thirty days.

In any of the foregoing aspects, the diabetes is type 2 diabetes. In certain embodiments, the subject is obese or overweight.

In any of the foregoing aspects, the method may further include a lifestyle modification or a dietary intervention prior to, during, or subsequent to administration of the composition. In some embodiments, the lifestyle modification includes an increase in physical activity. In other embodiments, the dietary intervention includes a low-calorie diet or a very low calorie diet.

In any of the foregoing aspects, the method may further include the step of monitoring whether the subject experiences an improvement in a sign or symptom of diabetes. In certain embodiments, an improvement in a sign or symptom of diabetes is selected from the group consisting of decreased hunger, increased energy, decreased plasma glucose, decreased plasma triglyceride, increased insulin sensitivity, an improvement in body mass index, and improved renal and hepatic functions.

In any of the foregoing aspects, the composition (e.g., including a chemical uncoupler, or salt, or precursor thereof and L-carnitine, or a salt, or derivative thereof) may provide a synergistic effect in decreasing plasma glucose or decreasing plasma triglyceride and/or preventing weight gain, promoting weight loss/slimming, or treating or preventing the development of diabetes. Said synergistic effect is evident from the observation that both thermogenicity and weight loss rate (or slimming rate) markedly increased when monotherapy with tyrphostin 9 was superseded-ceteris paribus-by simultaneous administration of tyrphostin 9 and L-carnitine tartrate (see Example 3).

A third aspect of the invention features a kit including a chemical uncoupler or precursor or a salt thereof, and instructions for administering the chemical uncoupler or precursor or salt thereof to a subject to treat obesity, prevent weight gain, promote weight loss/slimming, or treat or prevent the development of diabetes. In some embodiments, the chemical uncoupler is a compound from Table 1 or a salt or precursor or derivative of a compound from Table 1. In preferred embodiments, the chemical uncoupler is tyrphostin 9, which is administered substantially simultaneously with L-carnitine or a salt or derivative thereof.

In certain embodiments, the kit further includes L-carnitine or derivative or a salt thereof and instructions for administering the L-carnitine or derivative or salt thereof simultaneously or sequentially with the chemical uncoupler or precursor or salt thereof to a subject to treat obesity, prevent weight gain, promote weight loss/slimming, or treat or prevent the development of diabetes.

In other embodiments, the kit may further include one or more therapeutic agent(s) selected from the group consisting of insulin, a sulfonylurea, a biguanide, an alpha-glucosidase inhibitor, a thiazolidinedione, a meglitinide, an antidiabetic agent, a statin, and a weight loss supplement.

In certain embodiments of any of the above aspects, the L-carnitine or derivative or a salt thereof is selected from the group consisting of: L-carnitine tartrate, L-carnitine chloride, L-carnitine bromide, L-carnitine orotate, L-carnitine acid aspartate, L-carnitine acid phosphate, L-carnitine fumarate, L-carnitine lactate, L-carnitine maleate, L-carnitine acid maleate, L-carnitine acid oxalate, L-carnitine acid sulfate, L-carnitine glucose phosphate, L-carnitine acid tartrate, L-carnitine iodate, L-carnitine aspartate, L-carnitine citrate, L-carnitine acid citrate, L-carnitine acid fumarate, L-carnitine glycerophosphate, L-carnitine mucate, L-carnitine oxalate, L-carnitine sulfate, L-carnitine trichloroacetate, L-carnitine trifluoroacetate, L-carnitine methanesulfonate, L-carnitine pamoate, L-carnitine acid pamoate, $C_{2-8}$ alkanoyl L-carnitines, $C_{2-8}$ alkanoyl L-carnitine chloride, $C_{2-8}$ alkanoyl L-carnitine bromide, $C_{2-8}$ alkanoyl L-carnitine orotate, $C_{2-8}$ alkanoyl L-carnitine acid aspartate, $C_{2-8}$ alkanoyl L-carnitine acid phosphate, $C_{2-8}$ alkanoyl L-carnitine fumarate, $C_{2-8}$ alkanoyl L-carnitine lactate, $C_{2-8}$ alkanoyl L-carnitine maleate, $C_{2-8}$ alkanoyl L-carnitine acid maleate, $C_{2-8}$ alkanoyl L-carnitine acid oxalate, $C_{2-8}$ alkanoyl L-carnitine acid sulfate, $C_{2-8}$ alkanoyl L-carnitine glucose phosphate, $C_{2-8}$ alkanoyl L-carnitine tartrate, $C_{2-8}$ alkanoyl L-carnitine acid tartrate, $C_{2-8}$ alkanoyl L-carnitine iodate, $C_{2-8}$ alkanoyl L-carnitine aspartate, $C_{2-8}$ alkanoyl L-carnitine citrate, $C_{2-8}$alkanoyl L-carnitine acid citrate, $C_{2-8}$ alkanoyl L-carnitine acid fumarate, $C_{2-8}$ alkanoyl L-carnitine glycerophosphate, $C_{2-8}$ alkanoyl L-carnitine mucate, $C_{2-8}$ alkanoyl L-carnitine orotate, $C_{2-8}$ alkanoyl L-carnitine oxalate, $C_{2-8}$ alkanoyl L-carnitine sulfate, $C_{2-8}$ alkanoyl L-carnitine trichloroacetate, $C_{2-8}$ alkanoyl L-carnitine trifluoroacetate, $C_{2-8}$ alkanoyl L-carnitine methanesulfonate, $C_{2-8}$ alkanoyl L-carnitine pamoate, and $C_{2-8}$ alkanoyl L-carnitine acid pamoate. In preferred embodiments, the composition includes from about 2 mg to about 200 mg of tyrphostin 9 or salt or precursor thereof and from about 50 mg to about 5000 mg of L-carnitine or salt or derivative thereof.

A fourth aspect of the invention features a method for preparing tyrphostin 9, the method may include providing 4-hydroxy-3,5 di-tert-butylbenzaldehyde and reacting the 4-hydroxy-3,5 di-tert-butylbenzaldehyde with malonodinitrile and an amine base catalyst, optionally in a solvent, such that the reacting produces tyrphostin 9.

In certain embodiments, the reacting is done by providing heat for about 1 hour. In other embodiments, the amine base catalyst is selected from a group consisting of ammonia, piperidine, pyridine, pyrrolidine, and sarcosine or addition salts thereof. In preferred embodiments, the addition salt is ammonium acetate. In still other embodiments, the solvent is selected from a group consisting of ethanol, methanol, and isopropanol. In preferred embodiments, the ethanol is anhydrous ethanol.

A fifth aspect of the invention features a synergistic composition comprising a chemical uncoupler, or precursor, or salt thereof and L-carnitine, or salt, or derivative thereof, wherein the weight-to-weight ratio of L-carnitine, or salt, or derivative thereof to chemical uncoupler, or precursor, or salt thereof is greater than 10 but smaller than 700 (e.g., 10, about 10.5, about 11, about 12, about 14, about 15, about 20, about 25, about 30, about 50, about 80, about 90, about 100, about 150, about 200, about 250, about 300, about 350, about 400, about 450, about 500, about 550, about 600, about 625, about 650, about 675, about 680, or about 690).

Definitions

The term "preventing," as used herein, refers to prophylactic treatment or treatment that prevents one or more symptoms or development of a disease, disorder, or condition described herein. Treatment can be initiated, for example, prior to or following an event that precedes the onset of the disease, disorder, or condition. Treatment that includes administration of a composition of the invention, or a unit dose pharmaceutical composition thereof, can be acute, short-term, or chronic. The doses administered may be varied during the course of preventive or therapeutic treatment.

By "treating" is meant subjecting a patient to a management regimen for the purpose of combating a disease or disorder and obtaining beneficial or desired results, such as clinical results. Beneficial or desired results can include, but are not limited to, improvement in quality of life; alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable.

By "preventing weight gain" is meant controlling, arresting, and reducing weight gain. By preventing weight gain, for example, at least one or more of the following is achieved: decrease or maintenance in body fat or body weight, decrease or maintenance of plasma triglyceride levels, cessation of weight gain, reduction in hyperglycemia, and/or decrease in incidence or severity of diabetes, or reduction in hyperlipidaemia, and/or hypertriglyceridemia.

By "promoting weight loss" is meant achieving a weight reduction in the subject. For example, the administration of a composition as described herein can result in a weight reduction of, for example, at least 1, 2, 3, 5, 10, 15, 20, 25, 30, 35, 40, 45, or up to 50% of the body weight (as measured prior to the administration of the composition to the subject, i.e., baseline body weight). In the context of the present invention, weight reduction encompasses also the maintenance of a subject's weight and also the maintenance of plasma triglyceride levels achieved after weight reduction.

By "preventing the development of diabetes" is meant controlling, arresting, and reducing the progression of diabetes at any stage of the disease. The term "diabetes" as used herein includes, but is not limited to, type I diabetes, also known as insulin-dependent, diabetes mellitus (IDMM), type II diabetes, also known as non-insulin-dependent diabetes mellitus (NIDDM), diabetes insipidus, gestational diabetes, and borderline diabetes (e.g., prediabetes).

By "L-carnitine derivative" is meant a chemical compound able to generate L-carnitine through chemical or enzymatic action, such as hydrolysis of an ester, in which the alcoholic hydrogen atom has been replaced by an acyl group.

By "salt of a chemical uncoupler" is meant any addition salt thereof (e.g., a salt that may be obtained by reacting the uncoupler with a pharmaceutically-acceptable acid) or any phenoxide or thiophenoxide salt obtainable by replacing an acidic phenolic (or thiophenolic) proton by a pharmaceutically-acceptable metal cation or ammonium or substituted ammonium or phosphonium or sulphonium cation.

By "tyrphostin 9 salt" is meant a chemical compound in which the phenolic proton of a tyrphostin 9 molecule has been replaced by a pharmaceutically-acceptable metal cation (such as sodium, potassium, calcium, or magnesium) or by an ammonium ion or a pharmaceutically-acceptable substituted ammonium, phosphonium, or sulphonium ion.

By "tyrphostin 9 derivative" or "tyrphostin 9 precursor" is meant a chemical compound (such as a phenolic ester) able to produce Tyrphostin 9 by chemical or enzymatic means.

By "slimming" is meant the process of becoming slim or slimmer through a decrease (e.g., a decrease of 2%, 5%, 10%, 15%, 20%, 25%, 30%, 40%, 50%, 55%, 60%, 70%, 80%, or 90%) of body dimensions (e.g., measurements of the bust, waist, and/or hips).

By "thermogenesis" is meant the stimulation of energy expenditure and heat production that is a result of the action of endogenous and/or exogenous uncoupling agents on mitochondria.

By "preventing body mass index (BMI) increase" is meant controlling, arresting, and/or reducing the BMI of a subject.

By "composition" is meant a system comprising a substance or more than one substance described herein and manufactured or sold as part of a therapeutic or prophylactic regimen for the treatment of disease in a mammal or to promote and maintain general health. Pharmaceutical compositions can be formulated, for example, for oral administration in unit dosage form (e.g., a tablet, capsule, caplet, gel cap, or syrup); for topical administration (e.g., as a cream, gel, lotion, or ointment); for intravenous administration (e.g., as a sterile solution or colloidal dispersion free of particulate emboli and in a solvent system suitable for intravenous use); or in any other formulation described herein.

By "effective amount" is meant an agent in an amount sufficient to effect beneficial or desired results, such as clinical results, and, as such, an "effective amount" depends upon the context in which it is being applied.

By "administration" or "administering" is meant a method of giving a dosage of a composition to a mammal so as to produce contact of the active ingredient(s) of said composition with its (their) site(s) of action. The preferred method of administration may depend on a variety of factors, e.g., the components of the composition and the nature and severity of the disease, disorder, or condition.

By administering "substantially simultaneously" is meant a method of giving a dosage of two or more compositions or two or more substances described herein (e.g., a chemical uncoupler and L-carnitine) to a subject substantially at the same time, together, or in combination.

By administering "sequentially" is meant a method of giving a dosage of two or more compositions or two or more substances one after the other (e.g., within 15 minutes, 30 minutes, one hour, two hours, three hours, four hours, five hours, six hours, seven hours, eight hours, nine hours, or ten hours). For example, sequential administration of a substance or composition described herein (e.g., a chemical uncoupler and L-carnitine) may include administering, for example, the chemical uncoupler within one hour, two hours, three hours, four hours, five hours, six hours, seven hours, eight hours, nine hours, or ten hours after administering the L-carnitine, or vice versa.

By "therapeutic agent" or "prophylactic agent" is meant one or more active agents (e.g., any of the compounds described herein) formulated together in a single composition or one or more active agents (e.g., any of the compounds described herein) administered in combination to the subject.

By "subject" is meant a human or non-human animal (e.g., a mammal, e.g., a dog, a cat, a monkey, a donkey, a horse, a cow, a pig, a mouse, a rat, etc.).

By "enteral" is meant administration that involves any part of the gastrointestinal tract. Enteral administration can include: by mouth (i.e., oral administration) in the form of tablets, capsules, or drops, by gastric feeding tube, duodenal feeding tube, or rectally.

By "topical" is meant administration that is local or systemic, particularly epicutaneous, inhalational, eye drops, and/or ear drops.

By "parenteral" is meant administering the composition of the invention by means other than oral intake, particularly by injection of a form of liquid into the body. Parenteral administration can include: intravenous, intra-arterial, intraosseous infusion, intra-muscular, intracerebral, intracerebroventricular, and subcutaneous administration.

By "chemical uncoupler" is meant a compound that can transport protons across membranes, and when protons are transported across the inner mitochondrial membrane, the ATP synthesis is bypassed. For example, a chemical uncoupler may be, but is not limited to, a compound listed in Table 1.

In some embodiments, through chemical uncoupling, most of the energy derived from glucose oxidation is released as heat, and cells must thus perform the oxidation of a much greater number of glucose molecules than under normal (basal) conditions in order to generate the same number of ATP molecules.

By "obese" or "overweight" is meant a subject whose body mass index (BMI) exceeds 30 kg/m$^2$.

By "lifestyle modification" is meant a change in a subject's typical routine to incorporate increased activity with the goal of weight loss, maintenance, or treating other health concerns. For example, lifestyle modification may be prescribed by a physician to treat obesity. A lifestyle modification can include, but is not limited to, increased exercise, decreased smoking, and/or involvement in a dietary plan.

By "monitoring" is meant to observe and determine the progress of a subject and whether the subject experiences an improvement in the condition under treatment. Monitoring may also be performed preceding or following the treatment. For example, monitoring herein is used to determine whether a subject experiences an improvement in a sign or symptom of diabetes.

By "synergistic effect" is meant when two or more active agents (e.g., any of the compounds described herein) are administered together and the resulting effect is greater than the additive effect of each agent when administered singularly to a subject treated using the compositions of this invention.

By "amine base catalyst" is meant an organic compound containing a basic nitrogen atom with a lone electron pair, which functions to increase the rate of a chemical reaction without undergoing any permanent chemical change. Representative amine base catalysts include, but are not limited to, ammonia, piperidine, pyridine, pyrrolidine, and sarcosine or salts thereof.

The term "L-carnitine salt," as used herein, represents those L-carnitine salts which are, within the scope of sound medical judgment, suitable for use in contact with the tissues of humans and animals without undue toxicity, irritation, allergic response, and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

As used herein, "about" refers to an amount ±25% of the recited value.

As used herein, "a" or "an" means "at least one" or "one or more" unless otherwise indicated. In addition, the singular forms "a", "an", and "the" include plural referents unless the context clearly dictates otherwise.

Other features and advantages of the invention will be apparent from the following detailed description, and from the claims.

DETAILED DESCRIPTION

We have discovered that a chemical uncoupler [e.g., tyrphostin 9 (also referred to as 3,5-di-tert-butyl-4-hydroxybenzylidene)-malononitrile)] in combination with L-carnitine provides a synergistic effect in decreasing weight, plasma glucose levels, and/or plasma triglycerides levels. We have also shown that a composition including tyrphostin 9 results in weight loss/slimming and a decrease in triglyceride levels when orally administered to a subject suffering from obesity and/or metabolic syndrome. Furthermore, we have shown that administration of tyrphostin 9 contributed to the stabilization of plasma glucose and plasma triglyceride levels in diabetic subjects. In addition, we provide herein a more convenient method of synthesis for tyrphostin 9 than is currently available in the art. Accordingly, the present invention features compositions including a chemical uncoupler (e.g., tyrphostin 9) alone and in combination with other therapeutic agents (e.g., L-carnitine) for use in treating obesity, preventing weight gain, promoting weight loss, or treating or preventing the development of diabetes.

Therapeutic Agents

Chemical Uncouplers

Known chemical uncouplers of oxidative phosphorylation include, but are not limited to, the compounds shown in Table 1 below and found in U.S. Patent Publication No. 2004-0138301, which is incorporated herein by reference. Such compounds are known to safely enhance mitochondrial respiration and may be useful in treating conditions benefiting from an increase in this metabolism, including obesity and diabetes, particularly type 2 diabetes. In some embodiments, uncouplers may also reduce insulin release from β-cells, which may be useful in the prevention of diabetes.

TABLE 1

| Compound # | Chemical Structure | Compound Name |
|---|---|---|
| 1 | 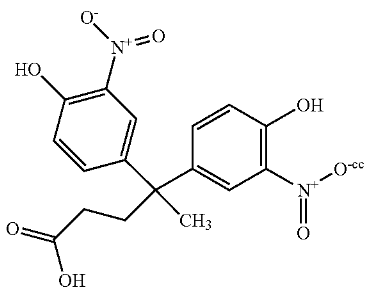 | 4,4-Bis-(4-Hydroxy-3-Nitrophenyl)-Valeric Acid |
| 2 | 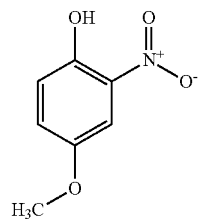 | 4-Methoxy-2-Nitrophenol |
| 3 | 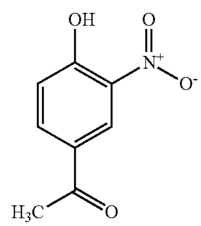 | 4-Hydroxy-3-Nitroacetophenone |
| 4 | 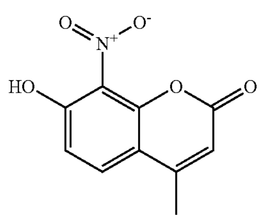 [SMILES: Cc1cc(=O)oc2c([N+](=O)[O-])c(O)ccc12] | 7-Hydroxy-4-Methyl-8-Nitro-Chromen-2-One |
| 5 | 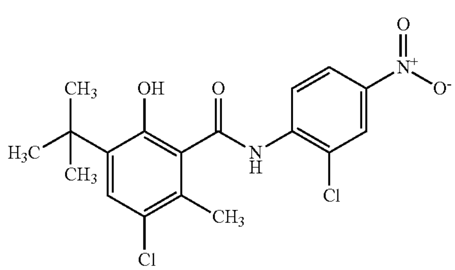 [SMILES: Cc1c(Cl)cc(C(C)(C)C)c(O)c1C(=O)Nc1ccc([N+](=O)[O-])cc1Cl] | 3-Tert-Butyl-5-Chloro-N-(2-Chloro-4-Nitrophenyl)-2-Hydroxy-6-Methyl-Benzamide |
| 6 | 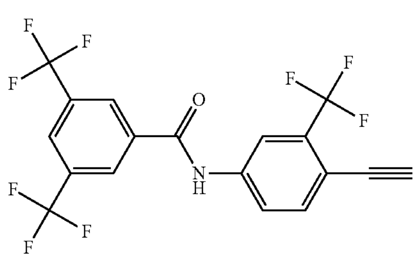 [SMILES: C#Cc1ccc(NC(=O)c2cc(C(F)(F)F)cc(C(F)(F)F)c2)cc1C(F)(F)F] | N-1-[4-Cyano-3-(Trifluoromethyl)Phenyl]-3,5-Di(Trifluoromethyl)Benzamide |

TABLE 1-continued

Chemical uncouplers of oxidative phosphorylation

| Compound # | Chemical Structure | Compound Name |
|---|---|---|
| 7 | 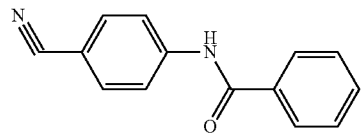 [SMILES: N#Cc1ccc(NC(=O)c2ccccc2)cc1] | N-(4-Cyanophenyl)Benzamide |
| 8 | 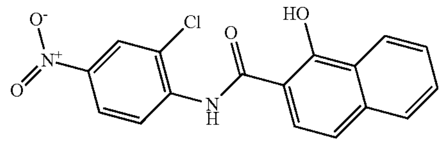 [SMILES: O=C(Nc1ccc([N+](=O)[O-])cc1Cl)c1ccc2ccccc2c1O] | 2'-Chloro-1-Hydroxy-4'-Nitro-2-Naphthanilide |
| 9 | 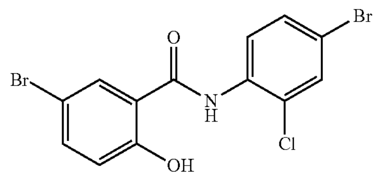 [SMILES: O=C(Nc1ccc(Br)cc1Cl)c1cc(Br)ccc1O] | N-(2-Chloro-4-Bromophenyl)-5-Bromosalicylanilide |
| 10 | 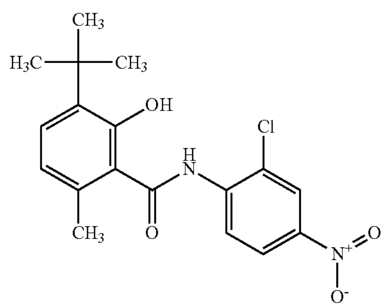 [SMILES: Cc1ccc(C(C)(C)C)c(O)c1C(=O)Nc1ccc([N+](=O)[O-])cc1Cl] | N-(2-Chloro-4-Nitrophenyl)-3-Tert-Butyl-6-Methylsalicylanilide |
| 11 | 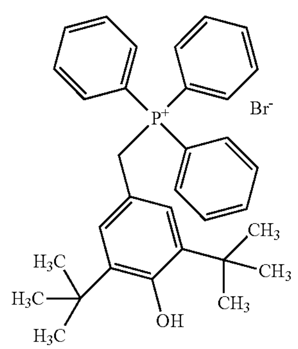 [SMILES: CC(C)(C)c1cc(C[P+](c2ccccc2)(c2ccccc2)c2ccccc2)cc(C(C)(C)C)c1O ; [Br-]] | (3,5-Di-Tert-Butyl-4-Hydroxybenzyl)Triphenylphosphonium Bromide |
| 12 | 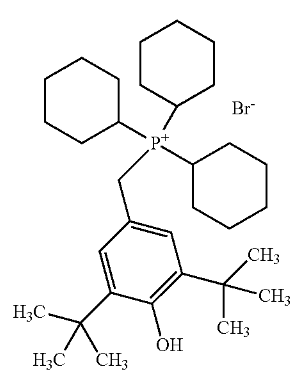 [SMILES: CC(C)(C)c1cc(C[P+](C2CCCCC2)(C2CCCCC2)C2CCCCC2)cc(C(C)(C)C)c1O ; [Br-]] | 3,5-Di-Tert-Butyl-4-Hydroxybenzyl)Tricyclohexylphosphonium Bromide |

TABLE 1-continued

Chemical uncouplers of oxidative phosphorylation

| Compound # | Chemical Structure | Compound Name |
|---|---|---|
| 13 | 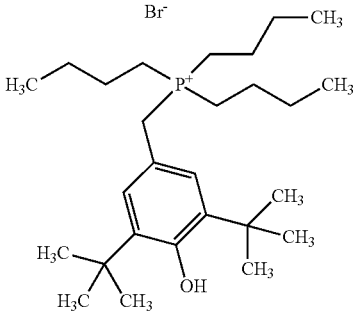 [SMILES: [Br-] ; CCCC[P+](CCCC)(CCCC)Cc1cc(C(C)(C)C)c(O)c(C(C)(C)C)c1] | (3,5-Di-Tert-Butyl-4-Hydroxybenzyl)Tributylphosphonium Bromide |
| 14 | 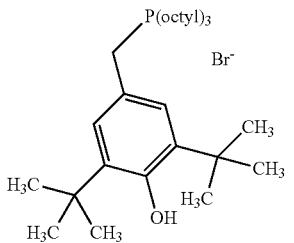 | (3,5-Di-Tert-Buty4-Hydroxybenzyl)Trioctylphosphonium Bromide |
| 15 | 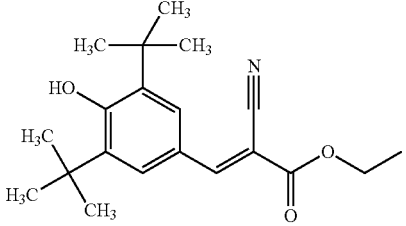 [SMILES: CCOC(=O)/C(C#N)=C/c1cc(C(C)(C)C)c(O)c(C(C)(C)C)c1] | 2-Cyano-3-(3,5-Di-Tert-Butyl-4-Hydroxyphenyl)-Acrylic Acid Ethyl Ester |
| 16 | 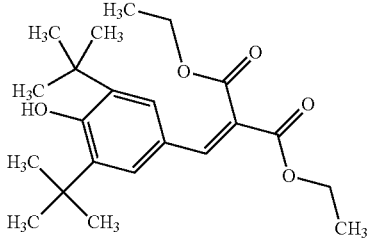 [SMILES: CCOC(=O)C(=Cc1cc(C(C)(C)C)c(O)c(C(C)(C)C)c1)C(=O)OCC] | 2-(3,5-Di-Tert-Butyl-4-Hydroxy-Benzylidene)-Malonic Acid Diethyl Ester |
| 17 | 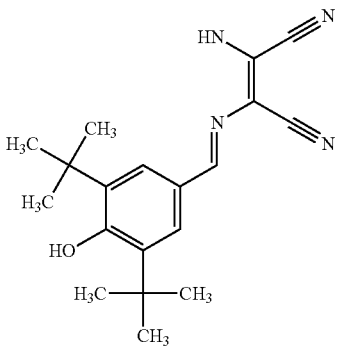 [SMILES: CC(C)(C)c1cc(/C=N/C(C#N)=C(\N)C#N)cc(C(C)(C)C)c1O] | 2-Amino-S-[(3,5-Di-Tert-Butyl-4-Hydroxybenzylidone)-Amino]-But-2-Enedinitrile |

TABLE 1-continued

Chemical uncouplers of oxidative phosphorylation

| Compound # | Chemical Structure | Compound Name |
|---|---|---|
| 18 | 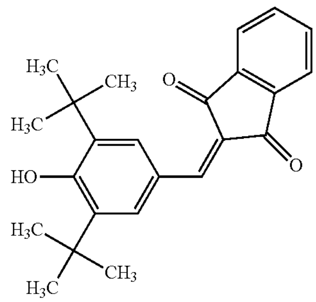 [SMILES: CC(C)(C)c1cc(C=C2C(=O)c3ccccc3C2=O)cc(C(C)(C)C)c1O] | 2-(3,5-Di-Tert-Butyl-4-Hydroxy-Benzylidene)-Indan-1,3-Dione |
| 19 | 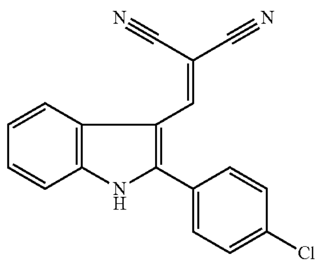 [SMILES: N#CC(C#N)=Cc1c(-c2ccc(Cl)cc2)[nH]c2ccccc12] | 2-[[2-(4-Chlorophenyl)-1H-Indol-3-Yl]Methylene]Malononitrile |
| 20 | 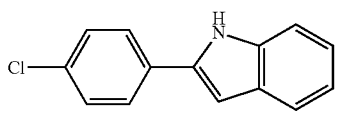 [SMILES: Clc1ccc(-c2cc3ccccc3[nH]2)cc1] | 2-(4-Chlorophenyl)-Indole |
| 21 | 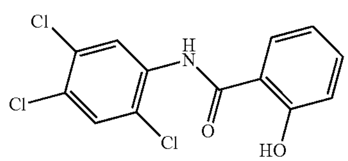 [SMILES: O=C(Nc1cc(Cl)c(Cl)cc1Cl)c1ccccc1O] | N-(2,4,5-Trichlorophenyl)Salicylanilide |
| 22 | 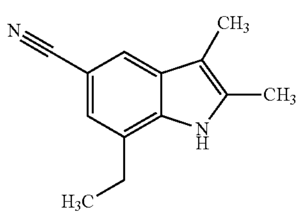 | 2,3-Dimethyl-5-Cyano-7-Ethylindole |
| 23 | 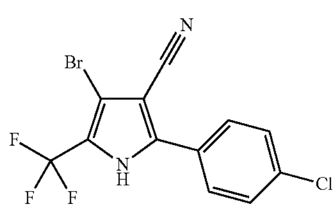 [SMILES: N#Cc1c(-c2ccc(Cl)cc2)[nH]c(C(F)(F)F)c1Br] | 4-Bromo-2-(4-Chlorophenyl)-5-Trifluoromethyl-1H-Pyrrole-3-Carbonitrile |
| 24 | 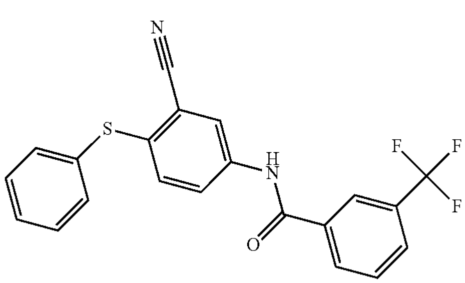 [SMILES: N#Cc1cc(NC(=O)c2cccc(C(F)(F)F)c2)ccc1Sc1ccccc1] | N-(3-Cyano-4-Phenylsulfanyl-Phenyl)-3-Trifluoromethyl-Benzamide |

TABLE 1-continued

Chemical uncouplers of oxidative phosphorylation

| Compound # | Chemical Structure | Compound Name |
| --- | --- | --- |
| 25 | 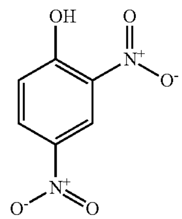 [SMILES: O=[N+]([O-])c1ccc(O)c([N+](=O)[O-])c1] | 2,4-Dinitrophenol |
| 26 | 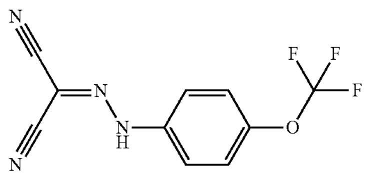 [SMILES: N#CC(C#N)=NNc1ccc(OC(F)(F)F)cc1] | Carbonylcyanide p-Trifluoromethoxy-Phenylhydrazone |
| 27 | 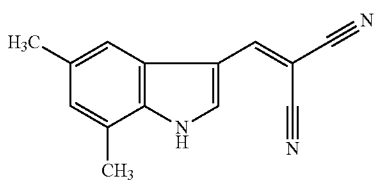 [SMILES: Cc1cc(C)c2[nH]cc(C=C(C#N)C#N)c2c1] | 2-(5,7-Dimethyl-1H-Indol-3-Ylmethylene)-Malononitrile |
| 28 | 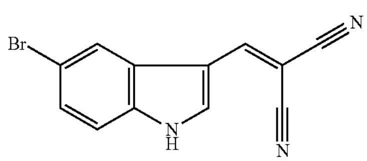 [SMILES: N#CC(C#N)=Cc1c[nH]c2ccc(Br)cc12] | 2-(5-Bromo-1H-Indol-3-Ylmethylene)-Malononitrile |
| 29 | 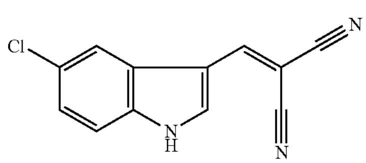 [SMILES: N#CC(C#N)=Cc1c[nH]c2ccc(Cl)cc12] | 2-((5-Chloro-1H-Indol-3-Yl)Methylene)Malononitrile |
| 30 | 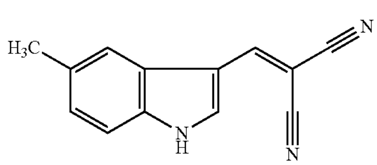 [SMILES: Cc1ccc2[nH]cc(C=C(C#N)C#N)c2c1] | 2-((5-Methyl-1H-Indol-3-Yl)Methylene)Malononitrile |
| 31 | 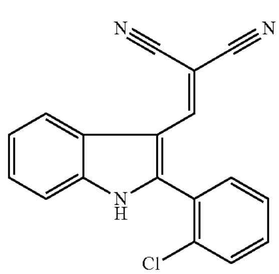 [SMILES: N#CC(C#N)=Cc1c(-c2ccccc2Cl)[nH]c2ccccc12] | 2-((5-Methyl-1H-Indol-3-Yl)Methylene)Malononitrile |

TABLE 1-continued

Chemical uncouplers of oxidative phosphorylation

| Compound # | Chemical Structure | Compound Name |
|---|---|---|
| 32 | 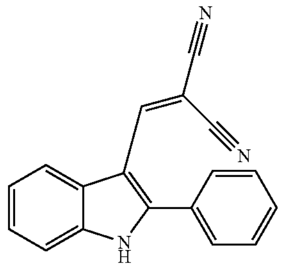 [SMILES: N#CC(C#N)=Cc1c(-c2ccccc2)[nH]c2ccccc12] | 2-(2-Phenyl-3-Indolylmethylene)-Malononitrile |
| 33 | 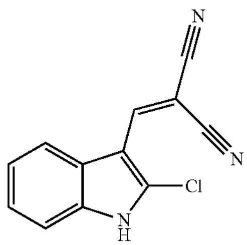 [SMILES: N#CC(C#N)=Cc1c(Cl)[nH]c2ccccc12] | 2-(2-Chloro-1H-Indol-3-Ylmethylene)-Malononitrile |
| 34 | 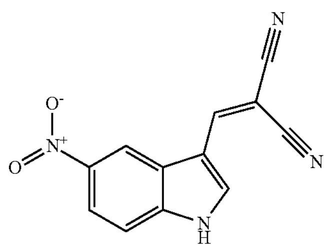 [SMILES: N#CC(C#N)=Cc1c[nH]c2ccc([N+](=O)[O-])cc12] | 2-(5-Nitro-1H-Indol-3-Ylmethylene)-Malononitrile |
| 35 | 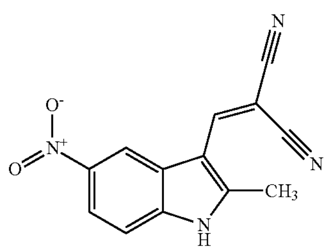 [SMILES: Cc1[nH]c2ccc([N+](=O)[O-])cc2c1C=C(C#N)C#N] | ] 2-(2-Methyl-5-Nitro-1H-Indol-3-Ylmethylene)-Malononitrile |
| 36 | 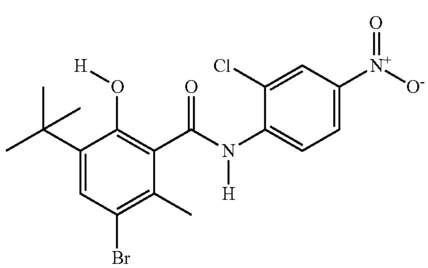 [SMILES: Cc1c(Br)cc(C(C)(C)C)c(O)c1C(=O)Nc1ccc([N+](=O)[O-])cc1Cl] | 3-Bromo-5-Tert-Butyl-N-(2-Chloro-4-Nitro-Phenyl)-6-Hydroxy-2-Methyl-Benzamide |
| 37 | 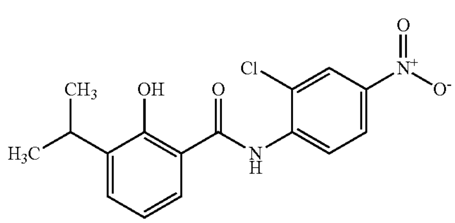 [SMILES: CC(C)c1cccc(C(=O)Nc2ccc([N+](=O)[O-])cc2Cl)c1O] | N-(2-Chloro-4-Nitro-Phenyl)-2-Hydroxy-3-Isopropyl-Benzamide |

TABLE 1-continued

Chemical uncouplers of oxidative phosphorylation

| Compound # | Chemical Structure | Compound Name |
|---|---|---|
| 38 | 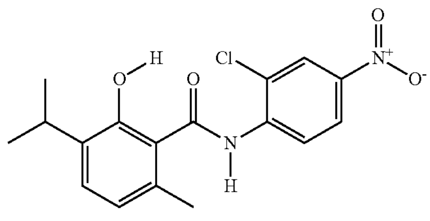 [SMILES: Cc1ccc(C(C)C)c(O)c1C(=O)Nc1ccc([N+](=O)[O-])cc1Cl] | N-(2-Chloro-4-Nitro-Phenyl)-2-Hydroxy-3-Isopropyl-6-Methyl-Benzamide |
| 39 | 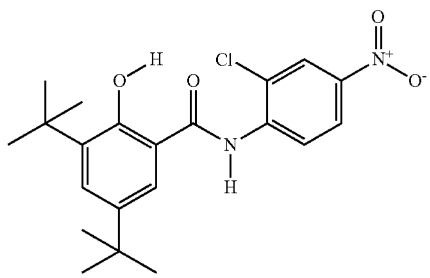 [SMILES: CC(C)(C)c1cc(C(=O)Nc2ccc([N+](=O)[O-])cc2Cl)c(O)c(C(C)(C)C)c1] | 3,5-Di-Tert-Butyl-N-(2-Chloro-4-Nitro-Phenyl)-2-Hydroxy-Benzamide |
| 40 | 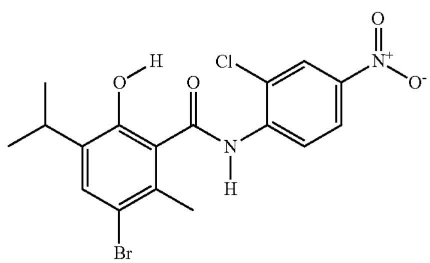 [SMILES: Cc1c(Br)cc(C(C)C)c(O)c1C(=O)Nc1ccc([N+](=O)[O-])cc1Cl] | 3-Bromo-N-(2-Chloro-4-Nitro-Phenyl)-6-Hydroxy-5-Isopropyl-2-Methyl-Benzamide |
| 41 | 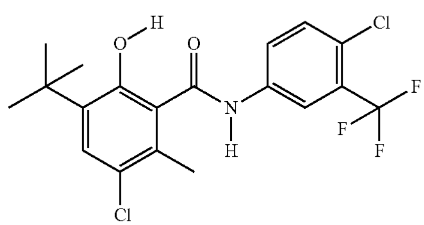 [SMILES: Cc1c(Cl)cc(C(C)(C)C)c(O)c1C(=O)Nc1ccc(Cl)c(C(F)(F)F)c1] | 3-Tert-Butyl-5-Chloro-N-(4-Chloro-3-Trifluoromethyl-Phenyl)-2-Hydroxy-6-Methyl-Benzamide |
| 42 | 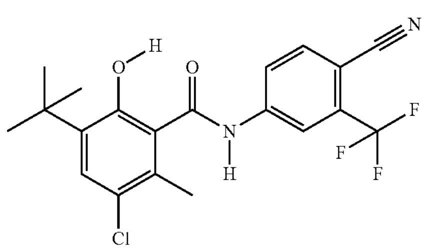 [SMILES: Cc1c(Cl)cc(C(C)(C)C)c(O)c1C(=O)Nc1ccc(C#N)c(C(F)(F)F)c1] | 3-Tert-Butyl-5-Chloro-N-(4-Cyano-3-Trifluoromethyl-Phenyl)-2-Hydroxy-6-Methyl-Benzamide |
| 43 | 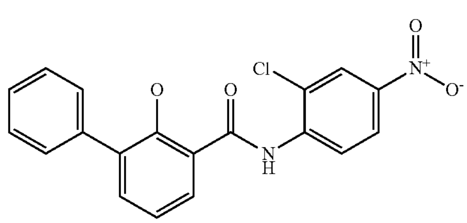 [SMILES: O=C(Nc1ccc([N+](=O)[O-])cc1Cl)c1cccc(-c2ccccc2)c1O] | 2-Hydroxy-Biphenyl-3-Carboxylic Acid (2-Chloro-4-Nitro-Phenyl)-Amide |

TABLE 1-continued

Chemical uncouplers of oxidative phosphorylation

| Compound # | Chemical Structure | Compound Name |
|---|---|---|
| 44 | 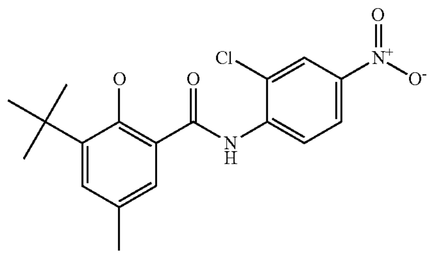 [SMILES: Cc1cc(C(=O)Nc2ccc([N+](=O)[O-])cc2Cl)c(O)c(C(C)(C)C)c1] | 3-Tert-Butyl-N-(2-Chloro-4-Nitro-Phenyl)-2-Hydroxy-5-Methyl-Benzamide |
| 45 | 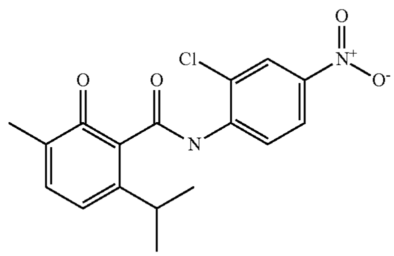 | N-(2-Chloro-4-Nitro-Phenyl)-2-Hydroxy-6-Isopropyl-3-Methyl-Benzamide |
| 46 | 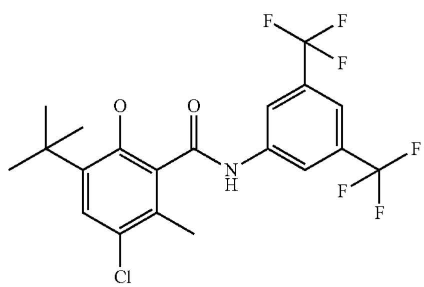 [SMILES: Cc1c(Cl)cc(C(C)(C)C)c(O)c1C(=O)Nc1cc(C(F)(F)F)cc(C(F)(F)F)c1] | N-(3,5-Bis-Trifluoromethyl-Phenyl)-3-Tert-Butyl-5-Chloro-2-Hydroxy-6-Methyl-Benzamide |
| 47 | 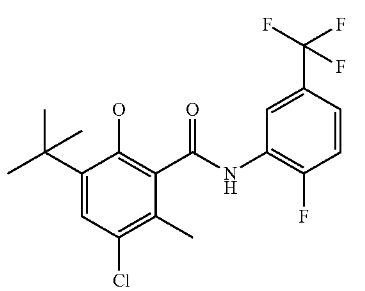 [SMILES: Cc1c(Cl)cc(C(C)(C)C)c(O)c1C(=O)Nc1cc(C(F)(F)F)ccc1F] | 3-Tert-Butyl-5-Chloro-N-(2-Fluoro-5-Trifluoromethyl-Phenyl)-2-Hydroxy-6-Methyl-Benzamide |
| 48 | 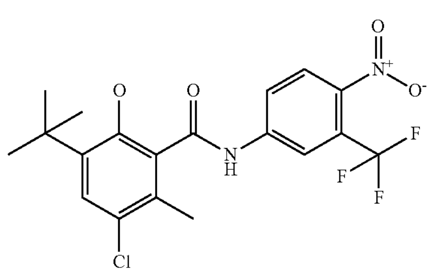 [SMILES: Cc1c(Cl)cc(C(C)(C)C)c(O)c1C(=O)Nc1ccc([N+](=O)[O-])c(C(F)(F)F)c1] | 3-Tert-Butyl-5-Chloro-2-Hydroxy-6-Methyl-N-(4-Nitro-3-Trifluoromethyl-Phenyl)-Benzamide |

TABLE 1-continued

Chemical uncouplers of oxidative phosphorylation

| Compound # | Chemical Structure | Compound Name |
|---|---|---|
| 49 | 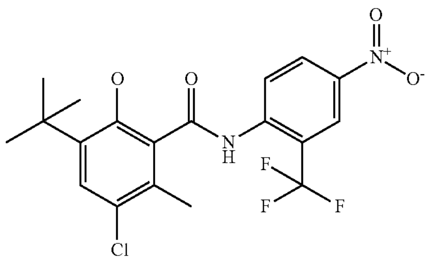 [SMILES: Cc1c(Cl)cc(C(C)(C)C)c(O)c1C(=O)Nc1ccc([N+](=O)[O-])cc1C(F)(F)F] | 3-Tert-Butyl-5-Chloro-2-Hydroxy-6-Methyl-N-(4-Nitro-2-Trifluoromethyl-Phenyl)-Benzamide |
| 50 | 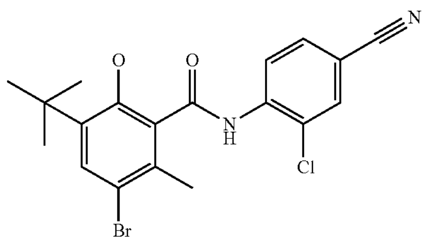 [SMILES: Cc1c(Br)cc(C(C)(C)C)c(O)c1C(=O)Nc1ccc(C#N)cc1Cl] | 3-Bromo-5-Tert-Butyl-N-(2-Chloro-4-Cyano-Phenyl)-6-Hydroxy-2-Methyl-Benzamide |
| 51 | 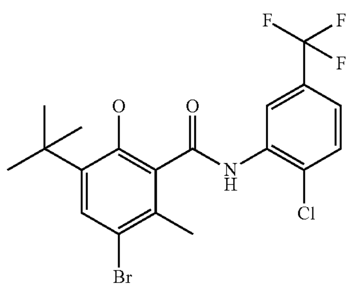 [SMILES: Cc1c(Br)cc(C(C)(C)C)c(O)c1C(=O)Nc1cc(C(F)(F)F)ccc1Cl] | 3-Bromo-5-Tert-Butyl-N-(2-Chloro-5-Trifluoromethyl-Phenyl)-6-Hydroxy-2-Methyl-Benzamide |
| 52 | 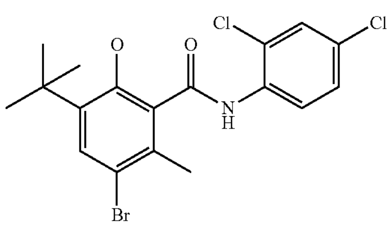 [SMILES: Cc1c(Br)cc(C(C)(C)C)c(O)c1C(=O)Nc1ccc(Cl)cc1Cl] | 3-Bromo-5-Tert-Butyl-N-(2,4-Dichloro-Phenyl)-6-Hydroxy-2-Methyl-Benzamide |
| 53 | 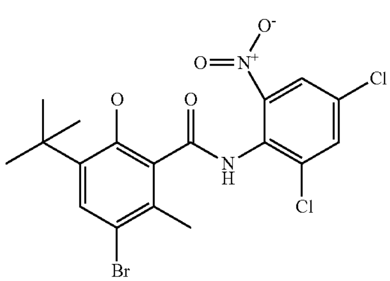 [SMILES: Cc1c(Br)cc(C(C)(C)C)c(O)c1C(=O)Nc1c(Cl)cc(Cl)cc1[N+](=O)[O-]] | 3-Bromo-5-Tert-Butyl-N-(2,4-Dichloro-6-Nitro-Phenyl)-6-Hydroxy-2-Methyl-Benzamide |

TABLE 1-continued

Chemical uncouplers of oxidative phosphorylation

| Compound # | Chemical Structure | Compound Name |
|---|---|---|
| 54 | 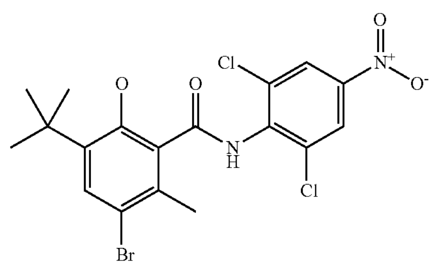 [SMILES: Cc1c(Br)cc(C(C)(C)C)c(O)c1C(=O)Nc1c(Cl)cc([N+](=O)[O-])cc1Cl] | 3-Bromo-5-Tert-Butyl-N-(2,6-Dichloro-4-Nitro-Phenyl)-6-Hydroxy-2-Methyl-Benzamide |
| 55 | 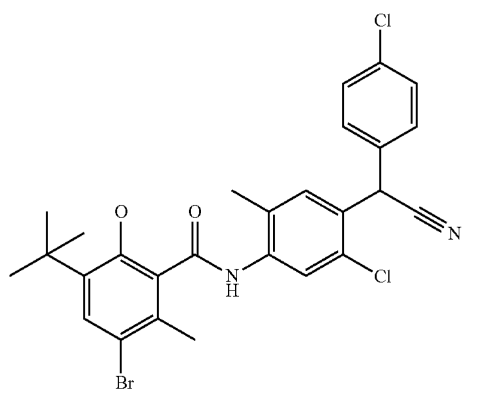 [SMILES: Cc1cc(C(C#N)c2ccc(Cl)cc2)c(Cl)cc1NC(=O)c1c(C)c(Br)cc(C(C)(C)C)c1O] | 3-Bromo-5-Tert-Butyl-N-{5-Chloro-4-[(4-Chloro-Phenyl)-Cyano-Methyl]-2-Methyl-Phenyl}-6-Hydroxy-2-Methyl-Benzamide |
| 56 | 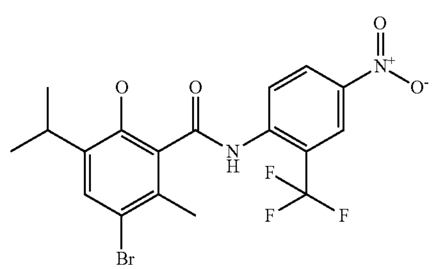 [SMILES: Cc1c(Br)cc(C(C)C)c(O)c1C(=O)Nc1ccc([N+](=O)[O-])cc1C(F)(F)F] | 3-Bromo-6-Hydroxy-5-Isopropyl-2-Methyl-N-(4-Nitro-2-Trifluoromethyl-Phenyl)-Benzamide. |
| 57 | 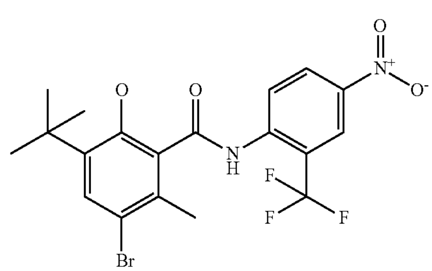 [SMILES: Cc1c(Br)cc(C(C)(C)C)c(O)c1C(=O)Nc1ccc([N+](=O)[O-])cc1C(F)(F)F] | 3-Bromo-5-Tert-Butyl-6-Hydroxy-2-Methyl-N-(4-Nitro-2-Trifluoromethyl-Phenyl)-Benzamide. |
| 58 | 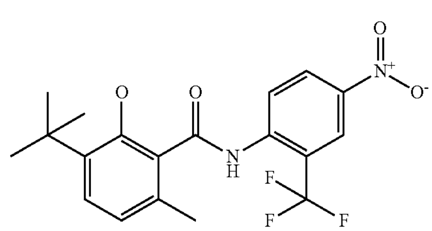 [SMILES: Cc1ccc(C(C)(C)C)c(O)c1C(=O)Nc1ccc([N+](=O)[O-])cc1C(F)(F)F] | 3-Tert-Butyl-2-Hydroxy-6-Methyl-N-(4-Nitro-2-Trifluoromethyl-Phenyl)-Benzamide |

TABLE 1-continued

Chemical uncouplers of oxidative phosphorylation

| Compound # | Chemical Structure | Compound Name |
|---|---|---|
| 59 | 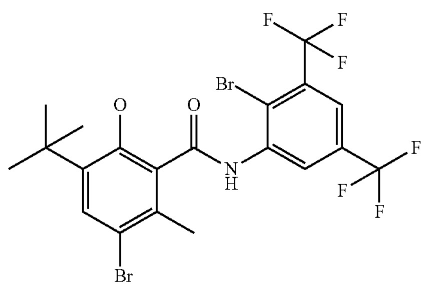 [SMILES: Cc1c(Br)cc(C(C)(C)C)c(O)c1C(=O)Nc1cc(C(F)(F)F)cc(C(F)(F)F)c1Br] | 3-Bromo-N-(2-Bromo-3,5-Bis-Trifluoromethyl-Phenyl)-5-Tert-Butyl-6-Hydroxy-2-Methylbenzamide |
| 60 | 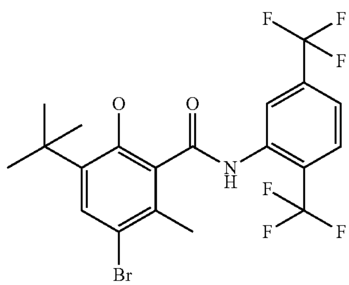 [SMILES: Cc1c(Br)cc(C(C)(C)C)c(O)c1C(=O)Nc1cc(C(F)(F)F)ccc1C(F)(F)F] | N-(2,5-Bis-Trifluoromethyl-Phenyl)-3-Bromo-5-Tert-Butyl-6-Hydroxy-2-Methyl-Benzamide |
| 61 | 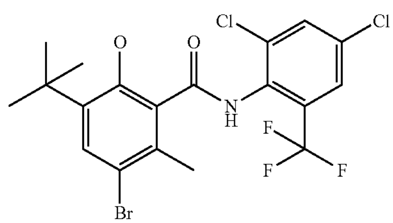 [SMILES: Cc1c(Br)cc(C(C)(C)C)c(O)c1C(=O)Nc1c(Cl)cc(Cl)cc1C(F)(F)F] | 3-Bromo-5-Tert-Butyl-N-(2,4-Dichloro-6-Trifluoromethyl-Phenyl)-6-Hydroxy-2-Methylbenzamide |
| 62 | 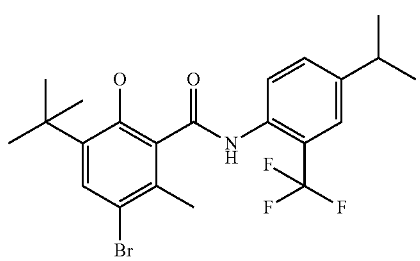 [SMILES: Cc1c(Br)cc(C(C)(C)C)c(O)c1C(=O)Nc1ccc(C(C)C)cc1C(F)(F)F] | 3-Bromo-5-Tert-Butyl-6-Hydroxy-N-(4-Isopropyl-2-Trifluoromethyl-Phenyl)-2-Methyl-Benzamide |
| 63 | 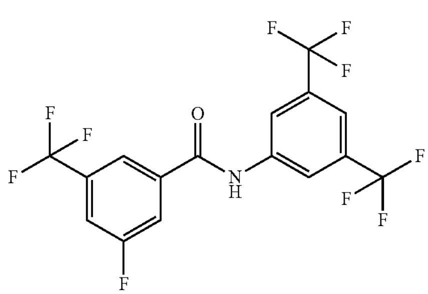 [SMILES: O=C(Nc1cc(C(F)(F)F)cc(C(F)(F)F)c1)c1cc(F)cc(C(F)(F)F)c1] | N-(3,5-Bis-Trifluoromethyl-Phenyl)-3-Fluoro-5-Trifluoromethyl-Benzamide |

TABLE 1-continued

Chemical uncouplers of oxidative phosphorylation

| Compound # | Chemical Structure | Compound Name |
|---|---|---|
| 64 | 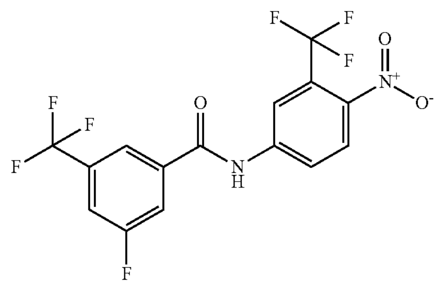 [SMILES: O=C(Nc1ccc([N+](=O)[O-])c(C(F)(F)F)c1)c1cc(F)cc(C(F)(F)F)c1] | 3-Fluoro-N-(4-Nitro-3-Trifluoromethyl-Phenyl)-5-Trifluoromethyl-Benzamide |
| 65 | 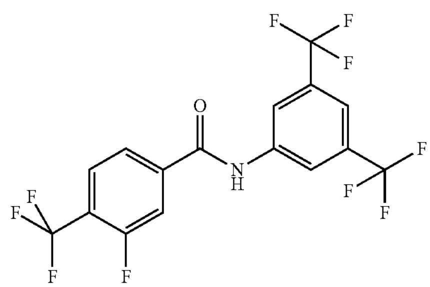 [SMILES: O=C(Nc1cc(C(F)(F)F)cc(C(F)(F)F)c1)c1ccc(C(F)(F)F)c(F)c1] | N-(3,5-Bis-Trifluoromethyl-Phenyl)-3-Fluoro-4-Trifluoromethyl-Benzamide |
| 66 | 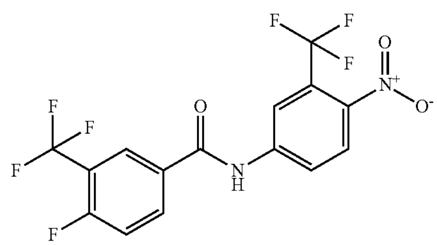 [SMILES: O=C(Nc1ccc([N+](=O)[O-])c(C(F)(F)F)c1)c1ccc(F)c(C(F)(F)F)c1] | 4-Fluoro-N-(4-Nitro-3-Trifluoromethyl-Phenyl)-3-Trifluoromethyl-Benzamide |
| 67 | 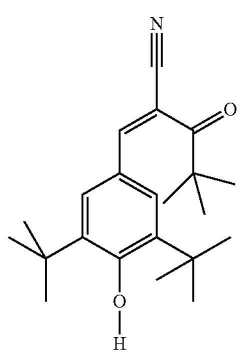 [SMILES: CC(C)(C)C(=O)/C(C#N)=C\c1cc(C(C)(C)C)c(O)c(C(C)(C)C)c1] | 3-(3,5-Di-Tert-Butyl-4-Hydroxy-Phenyl-2-(2,2-Dimethyl-Propionyl)-Acrylonitrile |
| 68 | 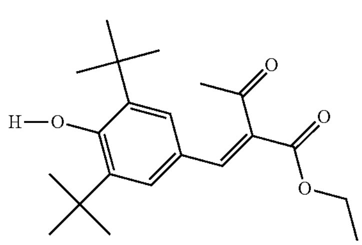 [SMILES: CCOC(=O)/C(=C/c1cc(C(C)(C)C)c(O)c(C(C)(C)C)c1)C(C)=O] | 2-Acetyl-3-(3,5-Di-Tert-Butyl-4-Hydroxy-Phenyl)-Acrylic Acid Ethyl Ester |

TABLE 1-continued

Chemical uncouplers of oxidative phosphorylation

| Compound # | Chemical Structure | Compound Name |
|---|---|---|
| 69 | 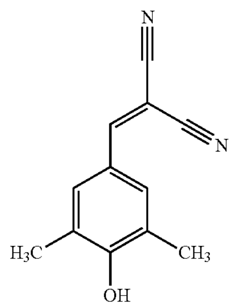 | 2-(3,5-Dimethyl-4-Hydroxy-Benzylidene)-Malononitrile |
| 70 | 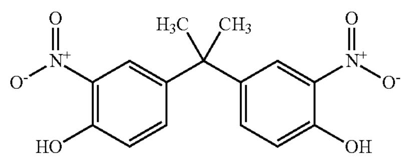 [SMILES: CC(C)(c1ccc(O)c([N+](=O)[O-])c1)c1ccc(O)c([N+](=O)[O-])c1] | 2-(3,5-Dimethyl-4-Hydroxy-Benzylidene)-Malononitrile |
| 71 | 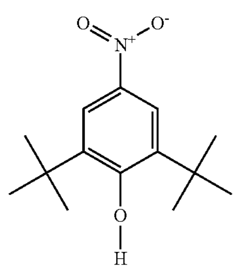 [SMILES: CC(C)(C)c1cc([N+](=O)[O-])cc(C(C)(C)C)c1O] | 2,6-Di-Tert-Butyl-4-Nitro-Phenol |
| 72 | 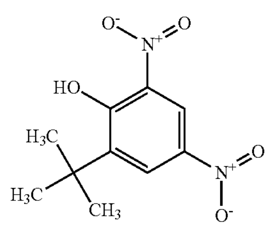 [SMILES: CC(C)(C)c1cc([N+](=O)[O-])cc([N+](=O)[O-])c1O] | 2-Tert-Butyl-4,6-Dinitro-Phenol |
| 73 | 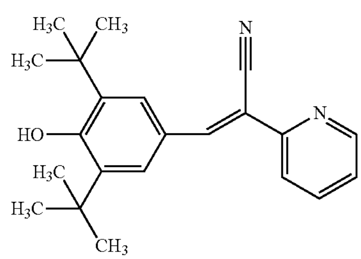 [SMILES: CC(C)(C)c1cc(/C=C(\C#N)c2ccccn2)cc(C(C)(C)C)c1O] | 3-(3,5-Di-Tert-Butyl-4-Hydroxy-Phenyl)-2-Pyridin-2-Yl-Acrylonitrile |
| 74 | 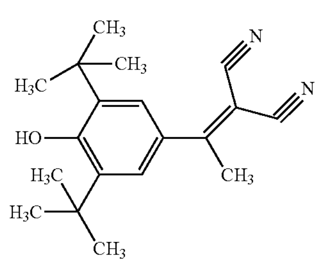 [SMILES: CC(=C(C#N)C#N)c1cc(C(C)(C)C)c(O)c(C(C)(C)C)c1] | 2-[1-(3,5-Di-Tert-Butyl-4-Hydroxy-Phenyl)-Ethylidene]-Malononitrile |

TABLE 1-continued

Chemical uncouplers of oxidative phosphorylation

| Compound # | Chemical Structure | Compound Name |
|---|---|---|
| 75 | 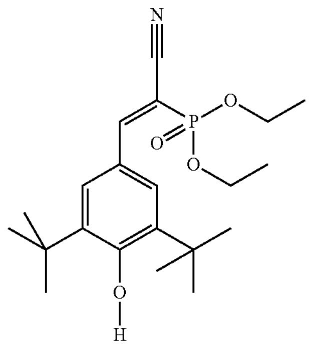 [SMILES: CCOP(=O)(OCC)/C(C#N)=C\c1cc(C(C)(C)C)c(O)c(C(C)(C)C)c1] | 3-(3,5-Di-Tertbutyl-4-Hydroxybenzylidene)-2-(Diethylphosphonate)-Propenenitrile |
| 76 | 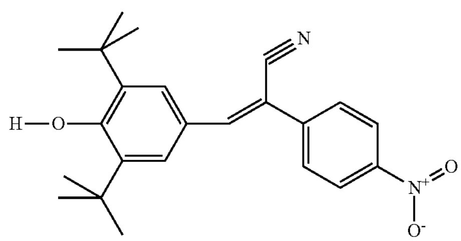 [SMILES: CC(C)(C)c1cc(/C=C(\C#N)c2ccc([N+](=O)[O-])cc2)cc(C(C)(C)C)c1O] | 3-(3,5-Di-Tert-Butyl-4-Hydroxy-Phenyl)-2-(4-Nitro-Phenyl)-Acrylonitrile |
| 77 | 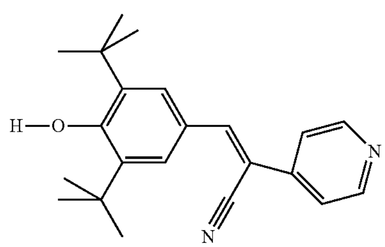 [SMILES: CC(C)(C)c1cc(/C=C(\C#N)c2ccncc2)cc(C(C)(C)C)c1O] | 3-(3,5-Di-Tert-Butyl-4-Hydroxy-Phenyl)-2-Pyridin-4-Yl-Acrylonitrile |
| 78 | 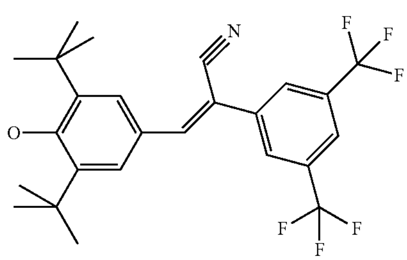 [SMILES: CC(C)(C)c1cc(/C=C(\C#N)c2cc(C(F)(F)F)cc(C(F)(F)F)c2)cc(C(C)(C)C)c1O] | 2-(3,5-Bis-Trifluoromethyl-Phenyl)-3-(3,5-Di-Tert-Butyl-4-Hydroxy-Phenyl)-Acrylonitrile |
| 79 | 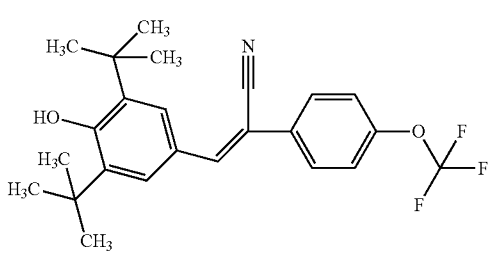 [SMILES: CC(C)(C)c1cc(/C=C(\C#N)c2ccc(OC(F)(F)F)cc2)cc(C(C)(C)C)c1O] | 3-(3,5-Di-Tert-Butyl-4-Hydroxy-Phenyl)-2-(4-Trifluoromethoxy-Phenyl)-Acrylonitrile |

TABLE 1-continued

Chemical uncouplers of oxidative phosphorylation

| Compound # | Chemical Structure | Compound Name |
|---|---|---|
| 80 | 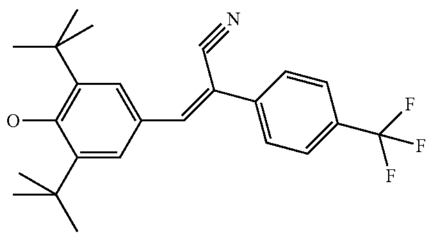 [SMILES: CC(C)(C)c1cc(/C=C(\C#N)c2ccc(C(F)(F)F)cc2)cc(C(C)(C)C)c1O] | 3-(3,5-Di-Tert-Butyl-4-Hydroxy-Phenyl)-2-(4-Trifluoromethyl-Phenyl)-Acrylonitrile |
| 81 | 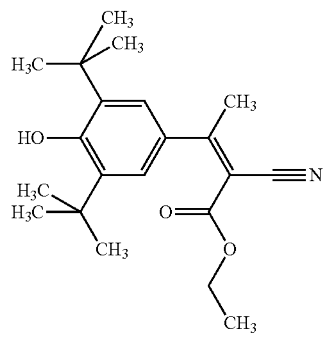 [SMILES: CCOC(=O)/C(C#N)=C(/C)c1cc(C(C)(C)C)c(O)c(C(C)(C)C)c1] | 2-Cyano-3-(3,5-Di-Tert-Butyl-4-Hydroxy-Phenyl)-But-2-Enoic Acid Ethyl Ester |
| 82 | 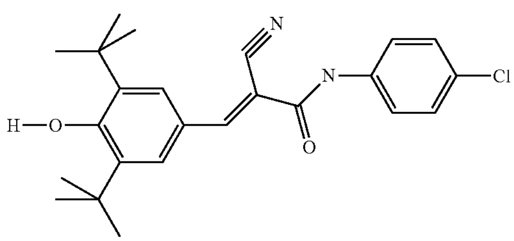 [SMILES: CC(C)(C)c1cc(/C=C(\C#N)C(=O)Nc2ccc(Cl)cc2)cc(C(C)(C)C)c1O] | N-(4-Chloro-Phenyl)-2-Cyano-3-(3,5-Di-Tert-Butyl-4-Hydroxy-Phenyl)-Acrylamide |
| 83 | 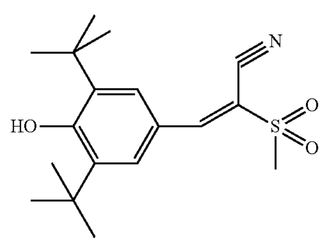 [SMILES: CC(C)(C)c1cc(/C=C(\C#N)S(C)(=O)=O)cc(C(C)(C)C)c1O] | (E)-3-(3,5-Di-Tert-Butyl-4-Hydroxy-Phenyl)-2-Methanesulfonyl-Acrylonitrile |
| 84 | 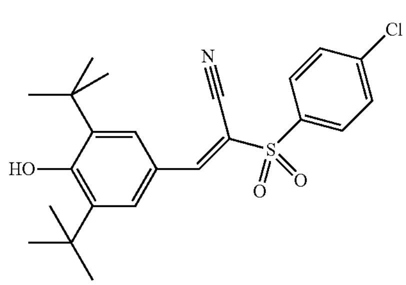 [SMILES: CC(C)(C)c1cc(/C=C(\C#N)S(=O)(=O)c2ccc(Cl)cc2)cc(C(C)(C)C)c1O] | (E)-2-(4-Chloro-Benzenesulfonyl)-3-(3,5-Di-Tert-Butyl-4-Hydroxy-Phenyl)-Acrylonitrile |

TABLE 1-continued

Chemical uncouplers of oxidative phosphorylation

| Compound # | Chemical Structure | Compound Name |
|---|---|---|
| 85 | 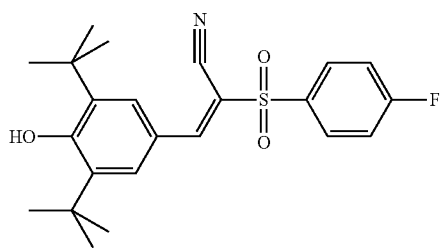 [SMILES: CC(C)(C)c1cc(/C=C(\C#N)S(=O)(=O)c2ccc(F)cc2)cc(C(C)(C)C)c1O] | (E)-3-(3,5-Di-Tert-Butyl-4-HydroxyPhenyl)-2-(4-Fluoro-Benzenesulfonyl)-Acrylonitrile |
| 86 | 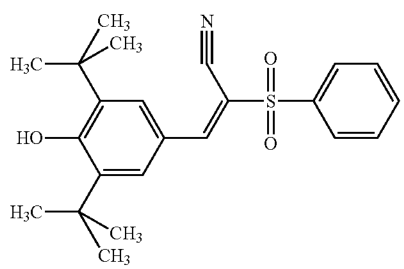 [SMILES: CC(C)(C)c1cc(/C=C(\C#N)S(=O)(=O)c2ccccc2)cc(C(C)(C)C)c1O] | (E)-2-Benzenesulfonyl-3-(3,5-Di-Tert-Butyl-4-Hydroxy-Phenyl)-Acrylonitrile |
| 87 | 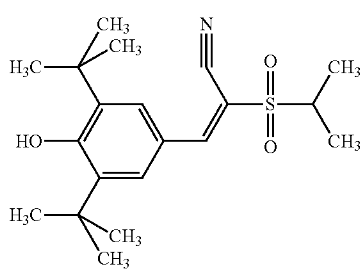 [SMILES: CC(C)S(=O)(=O)/C(C#N)=C/c1cc(C(C)(C)C)c(O)c(C(C)(C)C)c1] | (E)-3-(3,5-Di-Tert-Butyl-4-Hydroxy-Phenyl)-2-(Propane-2-Sulfonyl)-Acrylonitrile |
| 88 | 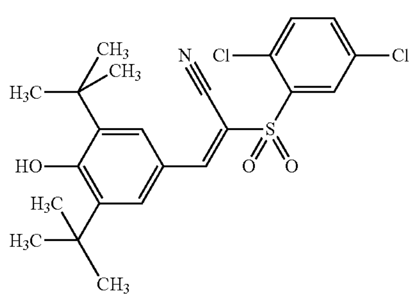 [SMILES: CC(C)(C)c1cc(/C=C(\C#N)S(=O)(=O)c2cc(Cl)ccc2Cl)cc(C(C)(C)C)c1O] | 3-(3,5-Di-Tert-Butyl-4-Hydroxy-Phenyl)-2-(2,5-Dichloro-Benzenesulfonyl)-Acrylonitrile |
| 89 | 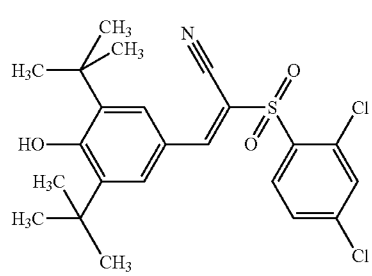 [SMILES: CC(C)(C)c1cc(/C=C(\C#N)S(=O)(=O)c2ccc(Cl)cc2Cl)cc(C(C)(C)C)c1O] | 3-(3,5-Di-Tert-Butyl-4-Hydroxy-Phenyl)-2-(2,4-Dichloro-Benzenesulfonyl)-Acrylonitrile |

TABLE 1-continued

Chemical uncouplers of oxidative phosphorylation

| Compound # | Chemical Structure | Compound Name |
| --- | --- | --- |
| 90 | 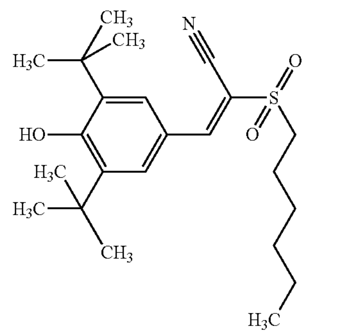 [SMILES: CCCCCCS(=O)(=O)/C(C#N)=C/c1cc(C(C)(C)C)c(O)c(C(C)(C)C)c1] | 3-(3,5-Di-Tert-Butyl-4-Hydroxy-Phenyl)-2-(Hexane-1-Sulfonyl)-Acrylonitrile |
| 91 | 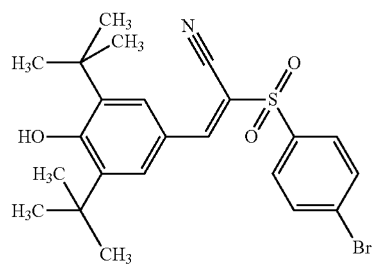 [SMILES: CC(C)(C)c1cc(/C=C(\C#N)S(=O)(=O)c2ccc(Br)cc2)cc(C(C)(C)C)c1O] | 2-(4-Bromo-Benzenesulfonyl)-3-(3,5-Di-Tert-Butyl-4-Hydroxy-Phenyl)-Acrylonitrile |
| 92 | 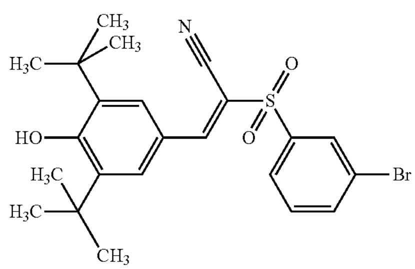 [SMILES: CC(C)(C)c1cc(/C=C(\C#N)S(=O)(=O)c2cccc(Br)c2)cc(C(C)(C)C)c1O] | 2-(3-Bromo-Benzenesulfonyl)-3-(3,5-Di-Tert-Butyl-4-Hydroxy-Phenyl)-Acrylonitrile |
| 93 | 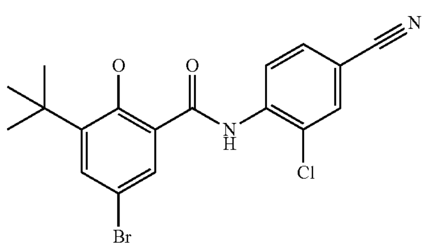 [SMILES: CC(C)(C)c1cc(Br)cc(C(=O)Nc2ccc(C#N)cc2Cl)c1O] | 5-Bromo-3-Tert-Butyl-N-(2-Chloro-4-Cyanophenyl)-2-Hydroxybenzamide |
| 94 | 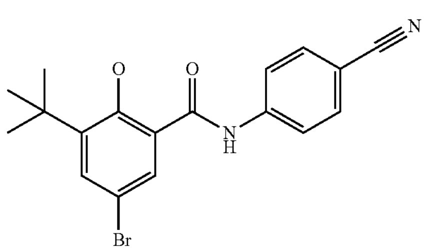 [SMILES: CC(C)(C)c1cc(Br)cc(C(=O)Nc2ccc(C#N)cc2)c1O] | 5-Bromo-3-Tert-Butyl-N-(4-Cyanophenyl)-2-Hydroxybenzamide |

TABLE 1-continued

Chemical uncouplers of oxidative phosphorylation

| Compound # | Chemical Structure | Compound Name |
|---|---|---|
| 95 | 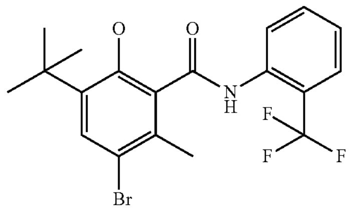 [SMILES: Cc1c(Br)cc(C(C)(C)C)c(O)c1C(=O)Nc1ccccc1C(F)(F)F] | 3-Bromo-5-Tert-Butyl-6-Hydroxy-2-Methyl-N-(2-Trifluoromethylphenyl)Benzamide |
| 96 | 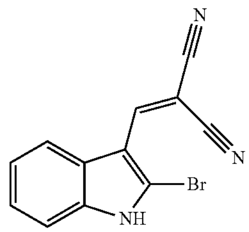 [SMILES: N#CC(C#N)=Cc1c(Br)[nH]c2ccccc12] | 2-(2-Bromo-1H-Indol-3-Ylmethylene)Malononitrile |
| 97 | 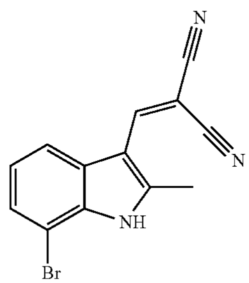 [SMILES: Cc1[nH]c2c(Br)cccc2c1C=C(C#N)C#N] | 2-(7-Bromo-2-Methyl-1H-Indol-3-Ylmethylene)Malononitrile |
| 98 | 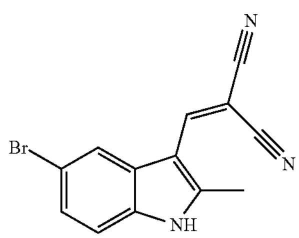 [SMILES: Cc1[nH]c2ccc(Br)cc2c1C=C(C#N)C#N] | 2-(5-Bromo-2-Methyl-1H-Indol-3-Ylmethylene)Malononitrile |

Tyrphostin 9

This invention features compositions including tyrphostin 9 (also referred to as 3,5-di-tert-butyl-4-hydroxybenzylidene) malononitrile), and derivatives or salts thereof. Tyrphostin 9 can act as a potent uncoupler of oxidative phosphorylation and an inhibitor of the differentiation of pre-adipocyte cells into mature adipocytes, thereby preventing the formation of adipocyte cells. Tyrphostin 9 has the structural molecular formula shown below:

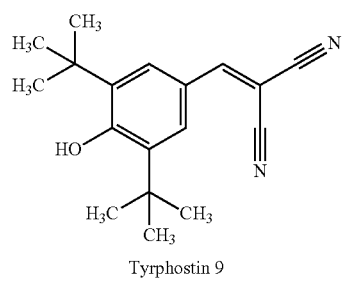 [SMILES: CC(C)(C)c1cc(C=C(C#N)C#N)cc(C(C)(C)C)c1O]

Tyrphostin 9

Tyrphostins are derivatives of benzylidenemalononitrile that decrease tyrosine phosphorylation, thereby affecting not a single mediator, but cell signaling transduction by tyrosine kinases. Tyrphostins have been intensively investigated as potential drugs for the treatment of inflammation-related and hyperproliferative diseases (Dimitrova P., Ivanovska N. *OA Inflammation* 1(1):4 (2013)). The physiological properties of Tyrphostin 9 are well known and it has been shown that this compound is a cytoprotectant of very low toxicity (in vitro and in vivo), which inhibits the TNF-induced respiratory burst of human neutrophils, but not their bactericidal activity, and that it may be beneficial in the treatment of conditions characterized by inappropriate vascular intimal hyperplasia. Furthermore, since many tyrphostins that are structurally very similar to tyrphostin 9 have been shown to strongly activate cytoprotective genes through induction of nuclear translocation of transcription factor Nrf2 (Turpaev K. et al, *Biochem. Pharmacol.* 82(5):535-47 (2010)), it is highly likely that tyrphostin 9 exerts cytoprotective effects through this pathway. Tyrphostin 9 and related benzylidene malonic acid derivatives may be obtained as outlined in Example 1 (see below).

The method of Example 1 may be used to prepare tyrphostin 9 and related compounds, which include, but are not limited to, 3,4-dihydroxybenzylidene-malononitrile, 3,5-dihydroxybenzylidene-malononitrile, 3-methoxy-4,5-dihydroxybenzylidenemalononitrile, 3,4,5-trihydroxybenzylidene-malononitrile, and 3-hydroxybenzylidene-malononitrile. The present invention also provides mixtures of tyrphostin 9, its derivatives, and one or more salts or derivatives of tyrphostin 9 in addition to mixtures of two or more salts or derivatives of tyrphostin 9. In some embodiments, variations of Example 1 may be used to obtain similar materials. Additional compositions of benzylidene- and cinnamylidene-malonic acid derivatives related to tyrphostin 9 are disclosed in European Patent Publication No. EP 0322738, which is herein incorporated by reference.

Tyrphostin 9 may also be obtained commercially through various chemical suppliers. For example, tyrphostin 9 is available from the following companies: RG-50872, Malonaben, SF 6847 (Santa Cruz Biotechnology), BML-E1215 (Enzo Life Sciences), ab141561 (Abcam), Sigma-T182 (Sigma-Aidrich), SF-6847 (Selleck Chemicals), and AG-17 (Cayman Chemical).

L-Camrnitine

The invention also features compositions including tyrphostin 9 with L-carnitine, derivatives, and salts thereof. L-carnitine and its salts may be useful in the treatment of cardiovascular diseases and in dietary supplements for weight loss. Without wishing to be bound by theory, L-carnitine may facilitate the metabolism of lipids. Compounds of the invention include, but are not limited to L-carnitine, salts of L-carnitine, alkanoyl L-carnitines, and salts of alkanoyl L-carnitine.

Suitable salts of L-carnitine and its derivatives include L-carnitine tartrate, L-carnitine chloride, L-carnitine bromide, L-carnitine acid aspartate, L-carnitine acid phosphate, L-carnitine fumarate, L-carnitine lactate, L-carnitine maleate, L-carnitine acid maleate, L-carnitine acid oxalate, L-carnitine acid sulfate, L-carnitine glucose phosphate, L-carnitine acid tartrate, L-carnitine iodate, L-carnitine aspartate, L-carnitine citrate, L-carnitine acid citrate, L-carnitine acid fumarate, L-carnitine glycerophosphate, L-carnitine mucate, L-carnitine orotate, L-carnitine oxalate, L-carnitine sulfate, L-carnitine trichloroacetate, L-carnitine trifluoroacetate, L-carnitine methanesulfonate, L-carnitine pamoate, L-carnitine acid pamoate, $C_{2-8}$ alkanoyl L-carnitines, $C_{2-8}$ alkanoyl L-carnitine chloride, $C_{2-8}$ alkanoyl L-carnitine bromide, $C_{2-8}$ alkanoyl L-carnitine orotate, $C_{2-8}$ alkanoyl L-carnitine acid aspartate, $C_{2-8}$ alkanoyl L-carnitine acid phosphate, $C_{2-8}$ alkanoyl L-carnitine fumarate, $C_{2-8}$ alkanoyl L-carnitine lactate, $C_{2-8}$ alkanoyl L-carnitine maleate, $C_{2-8}$ alkanoyl L-carnitine acid maleate, $C_{2-8}$ alkanoyl L-carnitine acid oxalate, $C_{2-8}$ alkanoyl L-carnitine acid sulfate, $C_{2-8}$ alkanoyl L-carnitine glucose phosphate, $C_{2-8}$ alkanoyl L-carnitine tartrate, $C_{2-8}$ alkanoyl L-carnitine acid tartrate, $C_{2-8}$ alkanoyl L-carnitine iodate, $C_{2-8}$ alkanoyl L-carnitine aspartate, $C_{2-8}$ alkanoyl L-carnitine citrate, $C_{2-8}$ alkanoyl L-carnitine acid citrate, $C_{2-8}$ alkanoyl L-carnitine acid fumarate, $C_{2-8}$ alkanoyl L-carnitine glycerophosphate, $C_{2-8}$ alkanoyl L-carnitine mucate, $C_{2-8}$ alkanoyl L-carnitine orotate, $C_{2-8}$ alkanoyl L-carnitine oxalate, $C_{2-8}$ alkanoyl L-carnitine sulfate, $C_{2-8}$ alkanoyl L-carnitine trichloroacetate, $C_{2-8}$ alkanoyl L-carnitine trifluoroacetate, $C_{2-8}$ alkanoyl L-carnitine methanesulfonate, $C_{2-8}$ alkanoyl L-carnitine pamoate, and $C_{2-8}$ alkanoyl L-carnitine acid pamoate.

The present invention also provides mixtures of L-carnitine and one or more salts of L-carnitine in addition to mixtures of two or more salts of L-carnitine. The present composition may further include any of the additional active ingredients that L-carnitine or salts thereof are known to be combined with in supplements, e.g., hydroxycitric acid, Co-enzyme Q10, chromium picolinate, gamma-linolenic acid, resveratrol, omega-3 acids, antioxidants, and/or vitamins, such as Vitamin B complex, Vitamin C, adrenal glandular extract, and pantothenic acid.

The present composition may further include powders or extracts or active principles of *Curcuma longa*, black currant, Bayberry bark, *Myrica cerifera*, black rice (*Oryza sativa* L. indica), *Camellia sinensis*, *Theobroma cacao*, *Emblica officinalis*, *Ilex paraguariensis*, *Cascara sagrada* bark, *Rhamnus purshiana*, *Acacia nilotica*, persimmon, Blueberry leaf, Grape seed, *Cordia salicifolia*, Saint John's Wort (*Hypericum perforatum*), *Pueruria thomsonn*, *Capparis spinosa*, *Gymnema sylvestre*, Elderberry, *Sambicus*, *Citrus aurantium*, Green coffee (*Coffea canefora*) bean, Jambolean (*Sygium cumini*), Rosemary (*Rosmarinus officinalis*), Ginger (*Zingiber officinalis*), *Cassia nomame*, *Cissus quadrangularis*, Apple, Cranberry, Rose Hips, White kidney bean (*Phaseolus vulgaris*), Licorice Root, Fenugreek, Yohimbe, White willow, *Cordyceps sinensis*, Ashwaganda, Astragalus, Gingseng, Schisandra, Siberian gingseng, Asian gingseng, Guggul (*Commiphora mukul*), Bitter melon (*Momordica charantia*), *Garcinia cambogia*, *Althaea officinalis*, *Bougainvillea spectabilis*, *Medicago sativa*, *Valeriana officinalis*, Damiana, chamomile, kava kava, passion flower, hops, skullcap, hawthorne, lavender, horse tail, dandelion. *Sambucus nigra*, *Uva ursi*, parsley, guarand, *Capsicum* genus, and *Allium* genus.

The present invention may further include calcium myristate, magnesium myristate, tetradecylthioacetic acid (TTA), thyroid hormones or their precursors, enhancers of thyroid function, Kreb's cycle metabolites, endogenous uncoupling protein(s), such as UCP-1, UCP-2, UCP-3, PUMP (plant uncoupling mitochondrial protein), or its (their) precursor(s), agonist(s), or enhancers, leucine, valine, isoleucine, glutamine, proline, tyrosine, conjugated linoleic acid, adrenaline secretion enhancers, fatty acids or esters, beta agonists, glucagon, arbutamine, vasopressin, ubiquinone, coenzyme 01, coenzyme Q2, melatonin, fatty acid esters of estrogens, such as oleylestrone, glucomannan, menthol, peppermint essential oil, thyme essential oil, elemental sulfur, and policosanols.

L-carnitine and salts thereof may be conveniently prepared by the methods described in U.S. Pat. Nos. 4,254,053; 4,602,039; 5,412,113; and 7,303,765, which are incorporated herein by reference.

The compositions of this invention may also be used in combination with compounds known to prevent weight gain, promote weight loss, or treat or prevent the development of diabetes, such as chemical uncouplers of oxidative phosphorylation, insulin, a sulfonylurea, a biguanide, an alpha-glucosidase inhibitor, a thiazolidinedione, a meglitinide, an antidiabetic agent, a statin, or a weight loss supplement.

Antidiabetic and Antiobesity Agents

Compositions of the present invention may be formulated and administered with suitable antidiabetic agents including insulin or insulin analogues and orally active hypoglycemic agents. Orally active hypoglycemic agents may include, but are not limited, to sulfonylureas, alpha-glucosidase inhibitors, thiazolidinediones, and meglitinides. Examples of pharmaceutically available sulfonylureas include acetohexamide, carbutamide, chlorpropamide, glibenclamide, glibornuride, gliclazide, glimepiride, glipizide, tolazamide, and tolbutamide. Examples of biguanides include Metformin (also referred to as N,N-Dimethylimidodicarbonimidic diamide or Glucophage), which is a common treatment for type 2 diabetes, particularly in overweight or obese subjects. Alpha-glucosidase inhibitors may be used to prevent the digestion of carbohydrates in subjects with diabetes and may include, but are not limited to, pharmaceutically available drugs such as Miglitol (also referred to as (2R,3R,4R,5S)-1-(2-hydroxyethyl)-2-(hydroxymethyl)piperidine-3,4,5-triol or Glyset) and Voglibose (also referred to as (1 S,2S,3R,4S,5S)-5-(1,3-dihydroxypropan-2-ylamino)-1-(hydroxymethyl)cyclohexane-1,2,3,4-tetraol). Examples of thiazolidinediones may include, but are not limited to, Rosiglitazone (also referred to as (RS)-5-[4-(2-[methyl(pyridin-2-yl) amino]ethoxy)benzyl]thiazolidine-2,4-dione or Avandia), Pioglitazone (also referred to as (RS)-5-(4-[2-(5-ethylpyridin-2-yl)ethoxy]benzyl)thiazolidine-2,4-dione or Actos), Lobeglitazone (also referred to as 5-[(4-[2-([6-(4-Methoxyphenoxy]pyrimidin-4-yl]-methylamino)ethoxy]phenyl) methyl]-1,3-thiazolidine-2,4-dione or Duvie), and Troglitazone (also referred to as (RS)-5-(4-[(6-hydroxy-2,5,7,8-tetramethylchroman-2-yl)methoxy]benzyl)thiazolidine-2,4-dione or Rezulin, Resulin, Romozin, or Noscal). Examples of meglitinides may include, but are not limited to, Repaglinide (also referred to as (S)-(+)-2-ethoxy-4-[2-(3-methyl-1-[2-(piperidin-1-yl)phenyl]butylamino)-2-oxoethyl]benzoic acid or Prandin), Nateglinide (also referred to as 3-phenyl-2-[(4-propan-2-ylcyclohexanecarbonyl)amino] propanoic acid or Starlix), and Mitiglinide (also referred to as (2S)-2-benzyl-4-[(3aR,7aS)-octahydro-2H-isoindol-2-yl]-4-oxobutanoic acid or Glufast). In some embodiments, compositions of the present invention may be formulated or administered with an antilipidemic agent, such as a statin or adjunct. Examples of statins include, but are not limited to, lovastatin, pravastatin, and simvastatin.

Weight Loss Supplements

One or more weight loss supplements safe for human consumption can be added to compositions of the present invention. These include naturally occurring, synthetic, or any combination of such substances. For example, supplements may include, but are not limited to, L-ornithine, L-tyrosine, L-tryptophan, L-phenylalanine, conjugated linoleic acid, gamma-linolenic acid, chromium picolinate, glucose tolerance factor, vanadyl sulfate, *Gymnema sylvestre*, bromelain, pancreatin, papain, coenzyme Q10, curcumin, barberry, bearberry, Silymarin, *Teucrium polium*, choline, inositol, human growth hormone, DHEA (dehydroepiandrosterone), caffeine, xanthenes (e.g., fucoxanthin), kola nut, psyllium, yerba mate, guarana, ginseng, medium chain triglycerides, hydroxycitric acid (HCA), kelp, lecithin, dihydroxyacetone, pyruvate, creatine, iodine, niacin, bladderwrack, white bean extract, glucomannan, chitosan, resveratrol, resveratrol derivatives, vitamin D, hCG, capsaicin, chia, hoodia, apple cider vinegar, coconut oil, bitter orange, and B vitamins.

Pharmaceutical Compositions and Formulations

A composition of the present invention can be administered by a variety of methods known in the art. As will be appreciated by the skilled artisan, the route and/or mode of administration will vary depending upon the desired results. The compositions can be formulated for parenteral, intranasal, topical, oral, or local administration, such as by a transdermal means, for prophylactic and/or therapeutic treatment. The compositions can be administered by oral ingestion, or by topical application, or parenterally (e.g., by intravenous, intramuscular, or subcutaneous injection), as discussed further below. Additional routes of administration include intravascular, intra-arterial, intratumoral, intraperitoneal, intraventricular, intraepidural, as well as nasal, ophthalmic, intrascleral, intraorbital, rectal, or aerosol inhalation administration.

Oral Administration

Formulations for oral use include tablets containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, and 6,372,218, hereby incorporated by reference). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or may be coated by known techniques, optionally to delay disintegration and absorption in the gastrointestinal tract and thereby providing a sustained action over a longer period. The coating may be adapted to release the compound in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols, and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed. The solid tablet compositions may include a coating adapted to protect the composition from unwanted chemical changes (e.g., chemical degradation prior to the release of the active substances). The coating may be applied on the solid dosage form in a similar manner as that described in Encyclopedia of Pharmaceutical Technology, supra.

The compositions of the invention may be mixed together in the tablet, or may be partitioned. In one example, a first agent is contained on the inside of the tablet, and a second agent is on the outside, such that a substantial portion of the second agent is released prior to the release of the first agent.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, kaolin, and/or any pharmaceutically acceptable excipient or additive), or as soft gelatin capsules, wherein the active ingredient is mixed with water or an oil medium, for example, peanut oil, liquid paraffin, or olive oil. Formulations for oral use may also be presented as sachets.

Formulations for oral use may additionally be presented as extended release or prolonged release formulations/unit dosage forms. Powders and granulates may be prepared using the ingredients mentioned above under tablets and capsules in a conventional manner using, e.g., a mixer, a fluid bed apparatus, or spray drying equipment. The compounds of the invention will be capable of extended shelf life in such combinations.

Topical Formulations

Pharmaceutical compositions according to the present invention can be formulated for topical administration. Subjects can be administered effective amounts of a compound described herein by means of topical application to the skin. The compositions of this invention may be formulated into a wide variety of product types that include, but are not limited, to solid and liquid compositions such as lotions, creams, gels, sticks, sprays, ointments, cleansing liquid washes and solid bars, shampoos, pastes, powders, foams, mousses, and wipes. These product types may contain several types of cosmetically acceptable topical or dermalogically acceptable carriers including, but not limited to, solutions, emulsions (e.g., microemulsions and nanoemulsions), gels, solids, and liposomes. Other carriers can be formulated by those of ordinary skill in the art.

The topical compositions useful in the present invention can be formulated as solutions. Solutions should preferably include an aqueous solvent (e.g., from about 50% to about 99.99% or from about 90% to about 99% of a cosmetically acceptable aqueous solvent). More preferably, such compositions should contain about 30% solvent, although this may vary dependent upon the formulation. Such solvents may include ethanol, propylene glycol, polyethylene glycol, mixtures thereof, and the like.

Topical compositions may also be formulated as a solution containing an emollient. Such compositions preferably contain from about 2% to about 50% of an emollient(s). As used herein, "emollients" refer to materials used for the prevention or relief of dryness and for the protection of the skin. A wide variety of suitable emollients are known and may be used herein. The International Cosmetic Ingredient Dictionary and Handbook, eds. Wenninger and McEwen, pp. 1656-61, 1626, and 1654-55 (The Cosmetic, Toiletry, and Fragrance Assoc, Washington, D.C., $7^{th}$ Edition, 1997) contains numerous examples of suitable materials. A lotion may be made from a solution. Lotions typically contain from about 1% to about 20% (more preferably, from about 5% to about 10%) of an emollient(s) and from about 50% to about 90% (more preferably, from about 60% to about 80%) of water. The compositions of the invention may be formulated as a cream. A cream typically comprises from about 5% to about 50% (more preferably, from about 10% to about 20%) of an emollient(s) and from about 45% to about 85% (more preferably, from about 50% to about 75%) of water. Yet another type of product that may be formulated from a solution is an ointment. An ointment may be constituted of a simple base of animal or vegetable oils or semi-solid hydrocarbons. An ointment may contain from about 2% to about 10% of an emollient(s), and from about 0.1% to about 2% of a thickening agent(s). The INCI Handbook, supra, contains a list of acceptable thickening agents or viscosity increasing agents useful in the compositions, methods, and kits of this invention.

The topical compositions useful in the present invention may also be preferably formulated as emulsions. If the carrier is an emulsion, from about 1% to about 10% (preferably from about 2% to about 5%) of the carrier should be made up of one or more emulsifiers. Emulsifiers may be nonionic, anionic or cationic. Suitable emulsifiers may be found in, e.g., the INCI Handbook, pp 0.1673-1686.

Lotions and creams may also be formulated as emulsions. Typically such lotions preferably contain from 0.5% to about 5% of an emulsifier(s). Such creams would typically comprise from about 1% to about 20% (preferably from about 5% to about 0%/o) of an emollient(s); from about 20% to about 80% (preferably, from 30% to about 70%) of water; and from about 1% to about 100/o (preferably, from about 2% to about 5%) of an emulsifier(s). Single emulsion skin care preparations, such as lotions and creams, of the oil-in-water type and water-in-oil type are well-known in the cosmetic art and are useful in the subject invention. Multiphase emulsion compositions, such as the water-in-oil-in-water type are also useful in the subject invention. In general, such single or multiphase emulsions contain water, emollients, and emulsifiers as essential ingredients.

The topical compositions of this invention may be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprise between about 0.1% and 5%, by weight, of such gelling agents. Microgels may be used to enhance follicular delivery of the formulations.

The compositions of the invention may contain one or more surfactants. In one embodiment, the composition may contain a lathering surfactant. A lathering surfactant is a surfactant that generates lather when combined with water and mechanically agitated. In one embodiment, the lathering surfactant has an initial foam height reading of at least 20 mm, such as at least 50 mm, in the Standard Test Method for Foaming Properties of Surface-Active Agents D1173-53 Set forth in the ASTM Annual Book of ASTM Standards 1001 Section 15 Volume 15.04 (using a concentration of 5 grams per liter, temperature of 49° C., and water hardness of 8 grains per gallon). Examples of lathering surfactants include, but are not limited to, anionic, nonionic, cationic, and amphoteric lathering surfactants. Nonlimiting examples of anionic lathering surfactants include those selected from the group consisting of sarcosinates, sulfates, isethionates, taurates, phosphates, lactylates, and glutamates. Specific examples include, but are not limited to, those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof. Nonlimiting examples of nonionic lathering surfactants include those selected from the group consisting of alkyl glucosides, alkyl polyglucosides, polyhydroxy fatty acid amides, alkoxylated fatty acid esters, lathering sucrose esters, amine oxides, and mixtures thereof. Specific examples include, but are not limited to, nonionic surfactants selected from the group consisting of C8-C14 glucose amides, C8-C14 alkyl polyglucosides, sucrose cocoate, sucrose laurate, lauramine oxide, cocoamine oxide, and mixtures thereof. Nonlimiting examples of amphoteric lathering surfactants, which also includes zwitterionic lathering surfactants, are those selected from the group consisting of betaines, sultaines, hydroxysultaines, alkyliminoacetates, iminodialkanoates, aminoalkanoates, and mixtures thereof. Nonlimiting examples of amphoteric surfactants of the present invention include disodium lauroamphodiacetate, sodium lauroamphoacetate, cetyl dimethyl betaine, cocoamidopropyl betaine, cocoamidopropyl hydroxy sultaine, and mixtures thereof.

The compositions according to this invention may further contain one or more additional cosmetically active agent(s) as well as the above-mentioned components. A cosmetically active agent is a compound, which may be a synthetic compound or a compound isolated, purified or concentrated from a natural source, or a natural extract containing a mixture of compounds, that has a cosmetic or therapeutic effect on the tissue, including, but not limited to: anti-microbial agents such as anti-yeast agents, anti-fungal, and anti-bacterial agents, anti-inflammatory agents, anti-aging agents, anti-parasite agents, external analgesics, sunscreens, photoprotectors, antioxidants, keratolytic agents, detergents/surfactants, moisturizers, nutrients, vitamins, minerals, energy enhancers, anti-perspiration agents, astringents, hair growth enhancing agents, hair coloring agents, pigments, firming agents, agents for skin conditioning, and odor-control agents such as odor masking or pH-changing agents. In one embodiment, the cosmetically active agent may be selected from, but not limited to, the group consisting of hydroxy acids, benzoyl peroxide, D-panthenol, octylmethoxycinnamate, titanium dioxide, octyl salicylate, homosalate, avobenzone, carotenoids, free radical scavengers, spin traps, retinoids such as retinoic acid (tretinoin) and retinoid precursors such as retinol and retinyl palmitate, vitamins such as vitamin E (alpha, beta, or delta tocopherols and/or their mixtures), ceramides, polyunsaturated fatty acids, essential fatty acids, enzymes, enzyme inhibitors, minerals, hormones such as progesterones, steroids such as hydrocortisone, 2-dimethylaminoethanol, metal (including, but not limited to, iron or zinc) salts such as copper chloride, peptides containing copper such as Cu:Gly-His-Lys, coenzyme Q10, amino acids, vitamins, acetyl-coenzyme A, niacin, riboflavin, thiamin, ribose, electron transporters such as NADH and FADH2, botanical extracts such as aloe vera, Feverfew, and Soy, and derivatives and mixtures thereof. The cosmetically active agent will preferably be present in the composition of the invention in an amount of from about 0.001% to about 20% by weight of the composition, more preferably, from about 0.005% to about 10% and most preferably, from about 0.01% to about 5%.

The compositions of this invention may also be formulated as suppositories (e.g. with bases such as cocoa butter and their glycerides) or retention enemas for rectal delivery.

Parenteral Compositions

A composition containing a compound described herein or identified using the methods of the invention may be administered parenterally by injection, infusion, or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and to which a suitable preservative may be added. The composition may be in the form of a solution, a suspension, an emulsion, an infusion device, or a delivery device for implantation. Alternatively, the composition may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Dosage

The compositions of the present invention are formulated into pharmaceutically acceptable dosage forms by conventional methods known to those of skill in the art. Actual dosage levels of the active ingredients in the compositions of the present invention may be varied so as to obtain an amount of the active ingredient which is effective to achieve the desired therapeutic or prophylactic response for a particular subject, composition, and mode of administration, without being toxic to the subject. The selected dosage level will depend upon a variety of pharmacokinetic factors including the activity of the particular compositions of the present invention employed, the route of administration, the time of administration, the rate of absorption of the particular agent being employed, the duration of the treatment, other drugs, substances, and/or materials used in combination with the particular compositions employed, the age, sex, weight, condition, general health and prior medical history of the subject being treated, and like factors well known in the medical arts. The dosage of any composition described herein may also depend on the amount or rate of weight loss desired, the severity or stage in the progression of diabetes, and the age, weight, and health of the subject to be treated.

A physician having ordinary skill in the art can readily determine and prescribe the effective amount of the composition required. For example, the physician can start doses of the substances of the invention employed in the composition at levels lower than that required in order to achieve the desired therapeutic effect and gradually increase the dosage until the desired effect is achieved. In general, a suitable daily dose of a composition of the invention will be that amount of the substance which is the lowest dose effective to produce a therapeutic or prophylactic effect. Such an effective dose will generally depend upon the factors described above. The compositions of the invention may conveniently be administered in unit dosage form and may be prepared by any of the methods well-known in the pharmaceutical art, for example, as described in "Remington: The Science and Practice of Pharmacy" (20th ed., ed. A. R. Gennaro, 2000, Lippincott Williams & Wilkins). Preferred therapeutic dosage levels are between about 2 mg to about 200 mg (e.g., 2, 4, 6, 8, 10, 20, 40, 60, 80, 100, 125, 150, 175, and 200 mg) of tyrphostin 9, derivatives, and salts thereof per dose administered to subjects with most of the symptoms, syndromes, and pathological conditions described herein. Preferred dosage levels are about 50 mg to about 5000 mg (e.g., 50, 60, 70, 80, 90, 100, 250, 500, 750, 1000, 2000, 3000, 4000, and 5000 mg) of L-carnitine and derivatives and salts thereof.

The composition may be administered to the subject in a single daily dose or in multiple doses. Administration may be one or multiple times daily, weekly (or at some other multiple day interval) or on an intermittent schedule, with that cycle repeated a given number of times (e.g., 2-10 cycles) or indefinitely. For example, a composition described herein may be administered once a day for, e.g., 2, 3, 4, 5, 6, 7, 8, 10, 15, 20, 25, 30 or more days. In another embodiment, a composition may be administered one or more times a day, e.g., 2, 3, 4, 5, 6, 7, 8, 9, 10, or more times a day. The composition can also be administered chronically, e.g., more than 30 days, e.g., 31 days, 40 days, 50 days, 60 days, 3 months, 6 months, 9 months, one year, two years, or three years). Preferably, compositions of the present invention will be administered for at least 30 days or more. During the first week of treatment, it is preferred that all subjects be administered a daily dose of about 10 mg Tyrphostin 9 and about 700 mg to about 1400 mg L-carnitine tartrate or L-carnitine fumarate; if by the end of said week, the subject fails to report increased body heat and/or increased sweating, the daily dose should be increased to 20 mg tyrphostin 9 and about 1400 to about 2800 mg L-carnitine fumarate or tartrate, taken at the same time.

Only in cases where no heat sensation or enhanced sweating is reported by the end of the second week should the daily dose be increased to about 30 mg tyrphostin 9 and about 2100 mg to about 4200 mg L-carnitine tartrate or fumarate. Only for exceptionally corpulent individuals should the effective dose be expected to exceed 30 mg tyrphostin 9 per day. Staying in a cool environment (at least when sweating or body temperature peaks) should be recommended, as well as staying hydrated and replenishing lost electrolytes. When an overdose is taken (as evidenced by an increased pulse rate and patient fatigue), appropriate support measures include cooling by uncovering the patient, spraying with tepid water, and fanning with an industrial grade fan. If cooling does not ensue, surface, auxiliary, and groin ice packs should immediately be applied as well as intravenous administration of cold glucose solutions and bicarbonate solution (1-2 mEq/kg). If the above measures fail, urine output should be corrected by mannitol administration and hypoglycemia by intravenous administration of 50% saturated glucose solution. When severe or persistent hypermetabolism cannot be corrected by the above measures, rectal propytthiouracil (1000 mg), hydrocortisone (100 mg for 6 h), or dexamethasone (2 mg for 6 h) should be intravenously administered. Patient agitation and restlessness can be avoided by an appropriate IV or IM dose of diazepam.

It is to be understood that, for any particular subject, specific dosage regimes should be adjusted over time according to the individual need and the professional judgment of the person administering or supervising the administration of the compound. For example, the dosage of a compound can be increased if the lower dose does not provide sufficient activity in promoting weight loss or treating diabetes. Conversely, the dosage of the compound can be decreased if there is improvement in weight loss or diabetes as assessed by the methods described herein. The compositions may be administered as symptoms occur or until the symptoms subside. Great efforts should be devoted to make patients fully aware of the observation that treatment success depends critically on the caloric input of their diet. If a patient's rate of weight gain at treatment onset is substantial, he/she should be explained that his/her weight can hardly be expected to diminish, unless his/her caloric input is significantly curtailed.

The compounds described herein may be optionally administered as a pharmaceutically acceptable salt, such as a non-toxic acid addition salt or metal complex that is commonly used in the pharmaceutical industry. Examples of acid addition salts include those derived from organic acids, such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids, such as tannic acid, carboxymethyl cellulose, or the like; and inorganic acids, such as hydrochloric acid, hydrobromic acid, sulfuric acid phosphoric acid, or the like. Metal complexes include zinc, iron, and the like.

The composition can be prepared by any useful method, as described above. For example, at least one therapeutic agent is dissolved in ethanol and added to a mixture of polyethylene glycols (PEGs). In another example, the composition further includes a skin penetrating enhancer such as a dimethyl alanine amide of medium chain fatty acids with carbon chains varying between C-12 and C-16. More specifically, active compounds alone or combinations thereof may be prepared in an ointment form or a cream form. The active compounds in the composition by weight would be in the range of 0.5% to 30% (w/w). The most preferred range would be between 5% and 20% (w/w). In another embodiment, the composition comprises between 0.5%-2%, 1%-2%, 2.5%-5%, 8%-12%, 10/%-20%, or 20-30% (w/w) of at least one compound (i.e., tyrphostin 9, derivatives, and salts thereof). In one implementation, the active compound is present in the composition in an amount of at least 0.5%, at least 1%, at least 2%, at least 2.5%, at least 3%, at least 5%, at least 10%, at least 15%, at least 20%, or at least 25% (w/w), and may be, for example, tyrphostin 9, derivatives, and salts thereof or L-carnitine and salts thereof.

Methods of Treatment

Obesity

The compounds and compositions described herein are useful for treating obesity. Obesity is a medical condition in which excess body fat has accumulated to the extent that it may have a negative effect on health, resulting in increased health problems. Obesity may be caused by a combination of excessive food intake, lack of physical activity, emotional issues, and genetic susceptibility as well as endocrine disorders, certain medications, or psychiatric illness. Individuals with obesity have an increased risk of many physical and mental conditions, and obesity has thus been found to reduce life expectancy. Nonlimiting examples of conditions associated with obesity include metabolic syndrome, type 2 diabetes, high blood pressure, high blood cholesterol, cardiovascular diseases, obstructive sleep apnea, certain types of cancer, osteoarthritis, asthma, hypertension, infertility, birth defects, polycystic ovarian syndrome, depression, gout, osteoarthritis, migraines, dementia, myocardial infarction, congestive heart failure, multiple sclerosis, and carpal tunnel syndrome. Obesity may further be characterized by high triglyceride levels in blood plasma and hyperglycemia, in which an excessive amount of glucose circulates in blood plasma. Accordingly, treatment with compositions of the present invention has been shown to not only promote weight loss, but also to normalize high blood glucose and high triglyceride plasma levels in obese or overweight subjects. Furthermore, since about 90% of obese subjects are also diabetic, the treatment methods of the present invention also encompass the population of obese subjects who are also diabetic.

Diabetes

The compounds and compositions described herein may be useful for treating or preventing the development of diabetes. Diabetes can be any metabolic disease in which a person has high blood sugar, either because the body does not produce enough insulin, or because cells do not respond to the insulin that is produced. Accordingly, treatment with compositions of the present invention has been shown to normalize high blood glucose levels in diabetic subjects. Non-limiting examples of diabetes includes, type 1 diabetes mellitus, type 2 diabetes mellitus, gestational diabetes, congenital diabetes, cystic fibrosis-related diabetes, steroid diabetes, latent autoimmune diabetes of adults, and monogenic diabetes. Complications associated with diabetes include but are not limited to hypoglycemia, diabetic ketoacidosis, non-ketotic hyperosmolar coma, cardiovascular disease, chronic renal failure, diabetic nephropathy, diabetic neuropathy, diabetes-related foot problems (e.g., diabetic foot ulcers), and diabetic retinopathy.

Obesity and Diabetes in Combination

The treatment methods for this patient population are essentially the same as those recommended for obese patients as detailed above.

Symptoms of Obesity and Diabetes

In some embodiments, subjects with obesity and/or diabetes are identified as candidates for treatment with the compositions described herein by symptoms of the disease, disorder, or conditions. In addition to the previously described associated disease risk (e.g., type 2 diabetes, hypertension, and cardiovascular disease), obese subjects may be categorized as having a BMI exceeding normal, e.g. greater than about 30 kg/m$^2$ (e.g., about 29, 31, 32, 33, 34, or 35 kg/m$^2$) and a higher than normal waist circumference, e.g., a waste circumference of greater than about 102 cm for a male (e.g., about 100, 101, 102, 103, 104, or 105 cm) or about 88 cm (e.g., about 86, 87, 89, 90, 91, or 92 cm) for a female. Additional physical conditions associated with obesity may include shortness of breath, feelings of tiredness, sore joints or muscles, skin problems, varicose veins, and irregular menstrual cycles. In some embodiments, obese subjects are identified by high plasma levels of triglycerides or the condition of hypertriglyceridemia, e.g., levels greater than about 150 mg/dL (e.g., about 148, 149, 151, 152, or 153 mg/dL). Obese subjects may further have higher than normal levels of plasma glucose when fasting, e.g., greater than about 100 mg/dL (e.g., about 98, 99, 101, 102, or 103 mg/dL). Further nonlimiting symptoms of obesity may include reduced HDL cholesterol, e.g., less than about 40 mg/dL (e.g., about 37, 38, 39, 41, or 42 mg/dL), and raised blood pressure, e.g., systolic blood pressure greater than about 130 mm Hg (e.g., about 127, 128, 129, 131, or 132 mm Hg). Furthermore, obese subjects may have previously been prescribed the treatment involving lifestyle modification, e.g., an increase in physical activity, and/or a dietary intervention, e.g., a low calorie or very low calorie diet, without improvements in the symptoms or condition of obesity.

Nonlimiting symptoms of diabetes (e.g., type 2 diabetes) include increased hunger and thirst, unexpected weight loss, decreased energy, decreased insulin sensitivity, an improvement in body mass index, and decreased renal function. In some embodiments, subjects with diabetes may be identified as individuals with elevated plasma glucose levels. Plasma glucose levels may be determined after fasting conditions with no food or liquids for a predetermined period. After fasting conditions and determination of plasma glucose levels, a subject with prediabetes (e.g., a subject with blood glucose levels higher than normal, but not high enough for diagnosis as diabetes) may have a blood glucose range of about 100 to about 125 mg/dL plasma glucose and a subject with type 2 diabetes may have a blood glucose range of greater than about 126 mg/dL plasma glucose (e.g., about 124, 125, 127, 128, 129, or 130 mg/dL). Alternatively, conditions of diabetes and prediabetes may be determined by administration of a standard amount of glucose, wherein the physician collects a blood sample before and approximately two to four hours after the subject ingests the glucose to determine glucose tolerance. Subjects with prediabetes may then have a blood glucose range of about 140 to about 199 mg/dL plasma glucose and a subject with type 2 diabetes may have a blood glucose range of greater than about 200 mg/dL plasma glucose (e.g., about 195, 196, 197, 198, 199, 121, or 122 mg/dL).

Patient Population

The subjects to be treated with the compositions of the invention can include, for example, subjects who are considered borderline diabetic (e.g., prediabetic, blood sugar level between 100-125 in fasting plasma glucose test, blood sugar level between 140-199 in oral glucose tolerance test, hemoglobin A1C of 5.7 to 6.4%), borderline overweight, diabetic, overweight, obese, or subjects who have a desire to maintain a healthy weight, prevent weight gain, or promote weight loss as well as subjects with both obesity and type 2 diabetes. Subjects who have a desire to maintain a healthy weight, prevent weight gain, or promote weight loss may be subjects who were previously obese and have undergone operative medical procedures (e.g., gastric bypass, laparoscopic adjustable gastric binding, biliopancreatic diversion, vertical banded gastroplasty) to reduce weight. Subjects who have a desire to maintain a healthy weight, prevent weight gain, or promote weight loss may also be healthy subjects considered within the scope of the invention (e.g., subjects who are not obese, overweight, prediabetic, or diabetic).

In some embodiments, the subjects to be treated with the compositions of the invention are also involved in lifestyle modifications and/or dietary interventions prior to, during, or subsequent to administration of the composition. The lifestyle modification can include, but is not limited to increase in physical activity (e.g., exercise), decrease in smoking, or participation in behavioral therapy. Dietary interventions can include participation in low calorie eating regiments, very low calorie eating regiments, portion controlled meals, avoidance of sugar/sweetened beverages.

Monitoring of Subjects

As described above, the compositions of the invention are administered for a time and in an amount sufficient to treat obesity, prevent weight gain, promote weight loss, or result in an improvement in a sign or symptom of diabetes. The methods of the invention can also include monitoring of weight loss or symptoms associated with the development of diabetes in response to treatment with the compositions of the invention. The monitoring of the condition can provide information on the state of the disorder or condition (e.g., worsening or improvement) to facilitate changes in treatment regime. The progression in weight gain, weight loss, and diabetes can also be monitored using the methods known in the art and described herein. Non-limiting examples of monitoring methods are determination of BMI and the measurement and detection of glucose and triglyceride plasma levels.

Quantitative methods for the analysis of weight loss or maintenance include measurements of BMI. In some embodiments, BMI may be monitored in the present invention by determining a subject's body mass and height and then dividing the individual's body mass by the square of their height, with the value given in units of $kg/m^2$. BMI may be further monitored using a table or from a chart which displays BMI as a function of mass and height using contour lines, or colors for different BMI categories. BMI values may range from underweight to obesity and may be used to assess how much a subjects body weight departs from what is normal or desirable for a person of his or her height. In some embodiments, the range of BMI may be about 25 $kg/m^2$ to about 30 $kg/m^2$ for overweight subjects and about 30 $kg/m^2$ to about 40 $kg/m^2$ for obese subjects. In one example, treatment or supplementation is administered or modified as previously described until BMI is lowered below the range for overweight or obese subjects and body weight is decreased by about 1, 2, 3, 5, 10, or 15%.

Quantitative methods for the analysis of improvements in the sign or symptom of diabetes or conditions associated with weight loss may include monitoring plasma glucose levels or plasma triglyceride levels. A blood glucose test may be performed by drawing blood from the subject and assaying the sample for glucose content. Typically, samples are collected by piercing the skin of the finger (the pinprick test). Continuous blood glucose monitoring (CGM) may be used to determine blood glucose levels at more frequent intervals by the placement of a sensor under the skin which communicates with a receiver configured to display or monitor the readings. Using the methods of the present invention, glucose levels may be reduced to normoglycemic levels after glucose administration and monitoring as described above, i.e., levels between 150 to 60 mg/dL, between 140 to 70 mg/dL, between 130 to 70 mg/dL, between 125 to 80 mg/dL, and preferably between 120 to 80 mg/dL. In some embodiments, average blood glucose levels may be monitored by using a HBA1c assay (A1c or glycosylated hemoglobin) to determine the amount of glycosylated hemoglobin A1c in blood plasma. In a diabetic subject, the amount may be about 6.5% or higher hemoglobin A1c (e.g., about 6.0, 6.1, 6.2, 6.3, 6.4, and or 6.6%/o). Using the methods of the present invention, glucose levels may be reduced to the normal range for a subject without diabetes, e.g., about 4% to about 5.6% hemoglobin A1c. Triglyceride levels may also be monitored using similar techniques to collect a blood sample after the subject has fasted for a predetermined period of about 9 to about 12 hours followed by assays to determine the lipid profile of the subject, which may include total cholesterol, LDL cholesterol, HDL cholesterol, and triglycerides. Using the methods of the present invention, triglyceride levels may be reduced to the normal range for subjects with diabetes or obesity, e.g., levels less than about 150 mg/dL (e.g., 146, 147, 148, 149, 151, or 152 mg/dL).

Kits

The compositions of the present invention can be used together with a set of instructions, i.e., to form a kit. The kit may include instructions for use of the compositions as a therapy as described herein. For example, the instructions may provide dosing and therapeutic regimes for use of the compounds of the invention to treat obesity, promote weight loss, promote slimming, reduce weight gain, or prevent or treat the development of diabetes in a subject in need thereof. Non-limiting examples include kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. The kit may be manufactured as a single use unit dose for one patient, multiple uses for a particular patient (at a constant dose or in which the individual compounds may vary in potency as therapy progresses), or the kit may contain multiple doses suitable for administration to multiple patients ("bulk packaging"). The kit components may be assembled in cartons, blister packs, bottles, tubes, and the like.

The following examples are intended to illustrate, rather than limit, the invention.

EXAMPLES

Example 1

Synthesis of Tyrphostin 9 and Related Benzylidenemalonic Acid Derivatives

A) 3 mole-g (703 g) of 4-hydroxy-3,5-di-tert-butylbenzaldehyde (99.1% pure, purchased from Yongyi Chemicals Group Co., Ltd, Changzhou, Jiangsu, China) and 2.5 L anhydrous ethanol are charged into a 5 L reactor provided with mechanical stirring and fitted with a reflux condenser.

B) 3 mole-g (198 g) of malonodinitrile (99.76% pure, purchased from Aceto Corporation, Port Washington, N.Y., USA) are quickly added to the reactor while stirring.

C) 75 g of ammonium acetate (98.5% pure, purchased from Fermont, Monterrey) are quickly added while stirring. The color of the reaction mixture goes from beige to yellow and then to orange.

D) The reactor is heated to reflux using a water bath. Reflux is first observed when the bath temperature reaches about 80° C. and is maintained during 1 hour. Complete solution is observed before reflux starts.

E) The water bath is removed and the temperature is allowed to drop to 50° C.

F) 1.5 L of water is added to the reaction mixture under brisk stirring. A precipitate appears.

G) The reaction mixture is cooled to 0° C.

H) The reaction mixture is filtered under reduced pressure using a Buchner funnel attached to a Kitasato flask.

I) The filter cake is thoroughly washed with water.

J) The wet filter cake is dried by heating in an oven at 60° C. until constant weight is achieved.

This procedure yields about 800 g (about 95% yield) of a light-yellow microcrystalline solid that melts at 141-142° C. (uncorrected), presents UV absorption maxima at 247 nm and 365 nm and has an Rf value of 0.65 (using benzene as eluant and Merck's TLC silica gel 60 $F_{254}$ plastic-backed sheets), with only one spot being observed. The mixed melting point of this compound and authentic tyrphostin 9 (acquired from Cayman Chemical) was also 141-142° C. (uncorrected), and its spectroscopic and chromatographic properties were identical to those of the authentic product. This compound is stable, with a shelf life of over 1 year at 25-35° C.; if necessary it may be recrystallized from ethanol.

Example 2

Preclinical Toxicity Studies and In Vivo Studies in C57BL/6 Mice

A preclinical toxicity study of tyrphostin 9 was conducted in human cell lines (brain, liver, lung, intestine, kidney, and muscle), followed by feeding experiments of C57BL/6 mice. In the in vivo mice experiments, the mice were orally administered tyrphostin 9 during 15 days, at a dose of 0.175 mg/kg/day. The results from these experiments showed the following:
  a) toxicity of tyrphostin 9 is low in all examined human cell lines
  b) tyrphostin 9 inhibits the differentiation of keratocytes into adipocytes
  c) tyrphostin 9 promotes—to a greater extent than taurosporine—adipocyte apoptosis mediated by caspase-3 and apoptosis induction is more evident in obese mice than in lean mice
  d) tyrphostin 9 promotes visceral lipid transport from adipocytes with concomitant reduction of adipocyte dimensions
  e) tyrphostin 9 promotes glycogen storage in hepatocytes
  f) tyrphostin 9 curtails (by about 50%) chow intake by obese mice grown on a high-fat diet, but has no such effect on lean mice
  g) mice treated with tyrphostin 9 (0.175 mg/kg/day) during 15 days showed no evidence of toxicity or inflammation, as judged by both histochemical and behavioral criteria.

Example 3

Preliminary Trials in Overweight, Obese, and Diabetic Subjects

A preliminary trial involving 75 overweight, obese, and/or diabetic subjects of both sexes was carried out over a twenty-month period. Exclusion criteria were: (1) recent significant weight gain, (2) a compromised thermoregulatory system, (3) pregnancy, (4) renal or hepatic failure, (5) use of illegal drugs or drugs that impair the body's heat dissipation mechanisms, (6) serious dysrhythmias, (7) unstable angina pectoris, (8) congestive heart failure, (9) severe cerebrovascular disease, (10) use of a pacemaker, (11) severe pulmonary impairment, (12) anemia, (13) Parkinson's disease, (14) body weight of less than 35 kilograms, (15) extensive psoriasis, (16) repeated episodes of hypoglycemia, (17) cystic fibrosis, (18) spinal cord injury, (19) a hereditary muscle disease, (20) chronic or recurrent venous thrombosis, (21) untreated hyperthyroidism, (22) exercise- or heat-induced angioedema, (23) seizure disorders, (24) schizophrenia, and (25) hypocalcemia.

Medications that reduce sweating, decrease vasodilatation, decrease cardiac output, or induce hypothalamic depression were not taken prior to, during, and immediately after treatment.

Obese participants, aged 16-72, were administered orally one or more hard gelatin capsules per day, each containing 20 mg of active ingredient (i.e., tyrphostin 9) and microcrystalline cellulose. They were instructed not to modify their food intake or to start a course of exercise. All participants were given only one capsule per day during the first week, at the end of which most of them reported sweating copiously and/or noticing a distinct increase in body temperature. Afterwards, different dosing schedules were imposed, with refractory individuals being administered two or three capsules per day (i.e., 40 or 60 mg tyrphostin 9 per day), whereas only one capsule per day was administered to all others, who consequently received 20 mg tyrphostin 9 per day throughout the trial. By the end of the trial, all participants (refractory and non-refractory) reported sweating copiously and/or experienced an increased heat sensation that usually fluctuated throughout the day and that frequently peaked after their main meal.

Participants were also instructed to prevent dehydration by drinking plenty of water and to replenish electrolytes by taking both potassium and magnesium supplements or V-8 Juice or Gatorade. Those receiving two capsules per day were asked to take them at the same time during weeks two and three and then to switch to one in the morning and one at night during weeks four and five. Participants receiving 40 mg tyrphostin 9 per day reported that sweating/body temperature peaked either during night time or day time, depending on whether the two capsules were taken in the morning or at night. Participants receiving two capsules simultaneously during weeks two and three and then switching to one in the morning and one at night reported that the sweating/heat sensation was more intense during weeks two and three. Obese participants lost on average 4 kg per month, with cumulative weight losses of up to 48 kg. Furthermore, treatment was usually very well tolerated, no "rebound effect" was observed, muscle mass loss was negligible, and no adverse effects were reported.

All participants experienced significant slimming by the end of treatment, i.e., significant reductions in waist circumference as well as other body measurements.

Diabetic subjects (mostly obese and all presenting Type 2 diabetes mellitus) were similarly treated. Among this group, treatment resulted in a significant decrease in blood glucose level, which could then be effectively managed, in some cases dispensing altogether with insulin or other antidiabetic agents. In both obese and diabetic subjects, the above treatment led to lower blood lipid values.

Example 4

Synergistic Effects of Tyrphostin 9 and L-Carnitine Tartrate

Obese subjects with similar BMI and whose weight had remained essentially constant during the past 30 days were recruited, instructed not to modify their eating habits, food intake, or lifestyle, and randomly and blindly assigned to either treatment Group A, Group B, or Group C.

Subjects in Group A were administered (orally) two capsules per day, each containing 20 mg Tyrphostin 9 plus inert excipient; subjects in Group B were administered (orally) four capsules per day, each containing 5 mg tyrphostin 9 and about 700 mg L-carnitine tartrate; subjects in Group C were administered—in the morning—two capsules, each containing 20 mg Tyrphostin 9 plus inert excipient, and—at night time—four capsules, each containing about 700 mg of L-carnitine tartrate. After 15 days, subjects in Group B exhibited the same weight loss (about 2 kg) as subjects in Group A, whereas subjects in Group C lost only about 1 kg on average.

After a two week washout period, a new experiment was initiated. Subjects in Group A were orally administered two capsules per day, each containing 20 mg Tyrphostin 9 plus inert excipient, subjects in Group B were given eight capsules per day, each containing 5 mg Tyrphostin 9 plus about 700 mg L-carnitine tartrate, and subjects in Group C were administered—in the morning—two capsules, each containing 20 mg tyrphostin 9 plus inert excipient and, at night, eight capsules each containing about 700 mg L-carnitine tartrate. After a 15-day treatment course, subjects in Group B lost about twice as much weight as subjects in Group A, with subjects in Group B reporting a much stronger thermogenic effect, whereas subjects in Group C had shed significantly less weight than those in Group B, but significantly more than members of Group A.

OTHER EMBODIMENTS

From the foregoing description, it is apparent that variations and modifications may be made to the invention described herein to adapt it to various usages and conditions. Such embodiments are also within the scope of the following claims.

All publications, patent applications, and patents mentioned in this specification are herein incorporated by reference to the same extent as if each independent publication, patent application, or patent was specifically and individually indicated to be incorporated by reference.

The invention claimed is:

1. A method for treating obesity without requiring a lifestyle modification or dietary intervention, said method consisting of administering about 20 mg to about 40 mg of tyrphostin 9 or salt thereof and about 2100 mg to about 5600 mg of L-carnitine tartrate within one hour of each other to a human subject in need thereof, wherein said administering is once daily for a duration sufficient for treating obesity.

2. The method of claim 1, wherein said tyrphostin 9 or salt thereof and said L-carnitine tartrate is administered for at least two weeks.

3. The method of claim 1, wherein administration of said tyrphostin 9 or salt thereof and said L-carnitine tartrate provides a decrease of plasma glucose or a decrease of plasma triglycerides.

* * * * *